US008425922B2

(12) United States Patent
Vajdy et al.

(10) Patent No.: US 8,425,922 B2
(45) Date of Patent: Apr. 23, 2013

(54) ADJUVANT COMPOSITIONS AND METHODS OF USE

(75) Inventors: Michael Vajdy, Orinda, CA (US); Shore Padrah, Orinda, CA (US)

(73) Assignee: EpitoGenesis, Inc., Walnut Creek, CA (US)

( * ) Notice: Subject to any disclaimer, the term of this patent is extended or adjusted under 35 U.S.C. 154(b) by 0 days.

(21) Appl. No.: 12/651,975

(22) Filed: Jan. 4, 2010

(65) Prior Publication Data

US 2010/0172941 A1 Jul. 8, 2010

Related U.S. Application Data

(60) Provisional application No. 61/204,316, filed on Jan. 5, 2009.

(51) Int. Cl.
*A61K 36/31* (2006.01)
*A61K 47/44* (2006.01)
*A61K 39/00* (2006.01)
*A61K 31/07* (2006.01)
*A61K 31/353* (2006.01)

(52) U.S. Cl.
USPC ......... 424/283.1; 424/755; 514/456; 514/725

(58) Field of Classification Search ........................ None
See application file for complete search history.

(56) References Cited

U.S. PATENT DOCUMENTS

| | | | |
|---|---|---|---|
| 4,698,221 A * | 10/1987 | Straub .................. | 424/245.1 |
| 5,135,855 A | 8/1992 | Moss et al. | |
| 5,139,941 A | 8/1992 | Muzyczka et al. | |
| 5,173,414 A | 12/1992 | Lebkowski et al. | |
| 5,219,740 A | 6/1993 | Miller et al. | |
| 5,229,130 A | 7/1993 | Sharma et al. | |
| 5,399,346 A | 3/1995 | Anderson et al. | |
| 5,580,859 A | 12/1996 | Felgner et al. | |
| 5,589,466 A | 12/1996 | Felgner et al. | |
| 5,614,413 A | 3/1997 | Morrow | |
| 5,676,950 A | 10/1997 | Small, Jr. et al. | |
| 6,063,384 A | 5/2000 | Morrow et al. | |
| 6,329,201 B1 | 12/2001 | Polo et al. | |
| 6,342,372 B1 | 1/2002 | Dubensky, Jr. et al. | |
| 2002/0071846 A1 * | 6/2002 | Deckers et al. ............ | 424/184.1 |
| 2003/0147898 A1 * | 8/2003 | Van Nest et al. ........... | 424/184.1 |
| 2006/0233816 A1 | 10/2006 | Schryvers et al. | |
| 2007/0082073 A1 * | 4/2007 | van Olphen et al. ......... | 424/729 |
| 2008/0254188 A1 | 10/2008 | Borowy-Borowski et al. | |

FOREIGN PATENT DOCUMENTS

| | | |
|---|---|---|
| EP | 0372501 | 6/1990 |
| EP | 0378881 | 7/1990 |
| EP | 0427347 | 5/1991 |
| EP | 0471177 | 2/1992 |
| WO | WO 89/03429 | 4/1989 |
| WO | WO 91/12882 | 9/1991 |
| WO | WO 92/01070 | 1/1992 |
| WO | WO 92/03545 | 3/1992 |
| WO | WO 92/19265 | 11/1992 |
| WO | WO 93/03769 | 3/1993 |
| WO | WO 93/13202 | 7/1993 |
| WO | WO 93/17712 | 9/1993 |
| WO | WO 94/26911 | 11/1994 |
| WO | WO 95/17211 | 6/1995 |
| WO | WO 96/29412 | 9/1996 |
| WO | WO 98/18928 | 5/1998 |
| WO | WO 98/58668 | 12/1998 |
| WO | WO 99/24578 | 5/1999 |
| WO | WO 99/27105 | 6/1999 |
| WO | WO 99/28475 | 6/1999 |
| WO | WO 99/36544 | 7/1999 |
| WO | WO 99/57280 | 11/1999 |
| WO | WO 00/22430 | 4/2000 |
| WO | WO 00/27994 | 5/2000 |
| WO | WO 00/37494 | 6/2000 |
| WO | WO 00/56360 | 9/2000 |
| WO | WO 00/61761 | 10/2000 |
| WO | WO 01/22993 | 4/2001 |
| WO | WO 01/52885 | 7/2001 |
| WO | WO 01/92552 | 12/2001 |
| WO | WO 02/02606 | 1/2002 |

OTHER PUBLICATIONS

Manesh et al. Effect of Naturally Occurring Isothiocyanates on the Immune System. Immunopharmacology and Immunotoxicology 25(3): 451-459 (2003).*
http://skipthepie.org/fats-and-oils/oil-mustard/compared-to/usda-commodity-food-oil-vegetable-soybean-refined/ (Retrieved on Jun. 17, 2011).*
Cejpek, et al. (1998) "Effect of Sulphite Treatment on Allyl Isothiocyanate in Mustard Paste" Food Chemistry 62 (1):53-57; Abstract; [online], [retrieved on Mar. 16, 2010]. Retrieved from the Internet: <URL:http://cat.inist.fr/?aModele=afficheN&cpsidt=2261722>ab.
Afzal, M., et al. (1984). "Protection of rams against epididymitis by a-vitamin E adjuvant vaccine." Veterinary Immunology and Immunopathology 7(3-4): 293-304.
Ala'Aldeen, D., et al (2001) "Unveiling of Genetic Basis of Resistance of *S Aureus* to Antibiotics" The Lancet 357(9264):1218-1219.
Athanassiades, T. (1981) "Adjuvant effect of vitamin A palmitate and analogs on cell-mediated immunity." Journal of the National Cancer Institute. 67(5):1153-6.
Ballow, M., et al. (1996). "Modulation of B-Cell Immunoglobulin Synthesis by Retinoic Acid." Clinical Immunology and Immunopathology 80(3): S73-S81.
Banic, S. (1982). "Immunostimulation by vitamin C." Int J Vitam Nutr Res Suppl. 23:49-52.
Bánvölgyi, A., G. Pozsgai, et al. (2004). "Mustard oil induces a transient receptor potential vanilloid 1 receptor-independent neurogenic inflammation and a non-neurogenic cellular inflammatory component in mice." Neuroscience 125(2): 449-459.
Barr, E., et al. (1994). "Efficient catheter-mediated gene transfer into the heart using replication-defective adenovirus." Gene Therapy 1(1): 51-58.
Barrnet, S., et al. (2008) "Protection of Macaques against Vaginal SHIV Challenge by Systemic or Mucosal and Systemic Vaccinations with HIV-Envelope" AIDS 22(3):339-348.
Bell, B. P. (2000). "Hepatitis A Vaccine." The Pediatric Infectious Disease Journal 19(12): 1187-1188.
Berkner, K.L. (1988). "Development of Adenovirus vector for the expression of heterologous genes." *BioTechniques* 6: 616-629.

(Continued)

*Primary Examiner* — Daniel Sullivan
*Assistant Examiner* — Peter Anthopolos
(74) *Attorney, Agent, or Firm* — Fitzpatrick, Cella, Harper & Scinto

(57) ABSTRACT

This disclosure provides adjuvant compositions that are capable of modulating the immune response in a subject. These adjuvant compositions may also be used enhance the immunogenicity of antigens. Also provided are methods of making the adjuvant compositions as well as methods of using the adjuvant compositions.

15 Claims, 10 Drawing Sheets

OTHER PUBLICATIONS

Bett, A. J., et al. (1993). "Packaging capacity and stability of human adenovirus type 5 vectors." J. Virol. 67(10): 5911-5921.

Bjune, G., et al.(1991). "Effect of outer membrane vesicle vaccine against group B meningococcal disease in Norway." Lancet 338(8775): 1093.

Boris-Lawrie, K. A. and H. M. Temin (1993). "Recent advances in retrovirus vector technology." Current Opinion in Genetics & Development 3(1): 102-109.

Budka, H. (1997) "The Human Prion Diseases: From Neuropathology to Pathobiology and Molecular Genetics" Neuropathol. Appl. Neurobiol. 23(5):416-422.

Burns, J. C., T. Friedmann, et al. (1993). "Vesicular stomatitis virus G glycoprotein pseudotyped retroviral vectors: concentration to very high titer and efficient gene transfer into mammalian and nonmammalian cells." Proceedings of the National Academy of Sciences of the United States of America 90(17): 8033-8037.

Carter, B. J. (1992). "Adeno-associated virus vectors." Current Opinion in Biotechnology 3:533-539.

Chen, X., Y. Li, et al. (1994). "A self-initiating eukaryotic transient gene expression system based on cotransfection of bacteriophage T7 RNA polymerase and DNA vectors containing a T7 autogene." Nucl. Acids Res. 22(11): 2114-2120.

Costantino, P., F. Norelli, et al. (1999). "Size fractionation of bacterial capsular polysaccharides for their use in conjugate vaccines." Vaccine 17(9-10): 1251-1263.

Dale, J. (1999). "Group A streptococcal vaccines." Infectious disease clinics of North America 13(1): 227-243.

Darmstadt, G., et al. (2003). "Neonatal Oil Massage." Indian Pediatrics 40(11): 1098-1099.

Darmstadt, G., et al. (2002). "Impact of topical oils on the skin barrier: possible implications for neonatal health in developing countries." Acta Paediatrica 91(5): 546-554.

Darmstadt, G., et al. (2002) "Traditional ractice of Oil Message of Neonates in Bangladesh" J. Health Popul. Nutr. 20(2):184-188.

Del Giudice, G., et al. (1998). "Molecular basis of vaccination." Molecular Aspects of Medicine 19(1): 1-70.

Deng, H., et al.(1994). "Self-amplifying expression from the T7 promoter in 3T3 mouse fibroblasts." GENE 143(2): 245-249.

Doe, B., et al. (1994). "Induction of HIV-1 envelope (gp120)-specific cytotoxic T lymphocyte responses in mice by recombinant CHO cell-derived gp120 is enhanced by enzymatic removal of N-linked glycans." European Journal of Immunology 24(10): 2369-2376.

Dreesen, D. W. (1997). "A global review of rabies vaccines for human use." Vaccine 15(Supplement 1): S2-S6.

Elroy-Stein, O. et al. (1990). "Cytoplasmic expression system based on constitutive synthesis of bacteriophage T7 RNA polymerase in mammalian cells." Proceedings of the National Academy of Sciences of the United States of America 87(17): 6743-6747.

Enioutina, E. Y., et al. (2000). "Enhancement of common mucosal immunity in aged mice following their supplementation with various antioxidants." Vaccine 18(22): 2381-2393.

Enioutina, E. Y., et al. (2000). "The induction of systemic and mucosal immune responses to antigen-adjuvant compositions administered into the skin: alterations in the migratory properties of dendritic cells appears to be important for stimulating mucosal immunity." Vaccine 18(24): 2753-2767.

Erickson, A., et al. (1993). "Hepatitis C virus-specific CTL responses in the liver of chimpanzees with acute and chronic hepatitis C." J Immunol 151(8): 4189-4199.

Ferretti, J. J., et al. (2001). "Complete genome sequence of an M1 strain of *Streptococcus pyogenes*." Proceedings of the National Academy of Sciences of the United States of America 98(8): 4658-4663.

Franchini, A., M., et al. (1991). "Vitamin E as adjuvant in emulsified vaccine for chicks." Poultry Sci. 70:1709-1715.

Franchini, A., et al. (1995) "Vitamin E in viral inactivated vaccines." Poultry Sci. 74: 666-671.

Fuerst, T. R., et al. (1986). "Eukaryotic transient-expression system based on recombinant vaccinia virus that synthesizes bacteriophage T7 RNA polymerase." Proceedings of the National Academy of Sciences of the United States of America 83(21): 8122-8126.

Fukasawa, et al. (1999). "*Neisseria meningitidis* serogroup C polysaccharide and serogroup B outer membrane vesicle conjugate as a bivalent meningococcus vaccine candidate." Vaccine 17(23-24): 2951-2958.

Gao, X., et al. (1994). "A Sustained, Cytoplasmic Transgene Expression System Delivered by Cationic Liposomes." Biochemical and Biophysical Research Communications 200(3): 1201-1206.

Gerlich, et al. (1990). "Eradication strategies for HBV: Discussion, part 1." Vaccine 8(Supplement 1): S79-S80.

Gerlich, et al. (1990). "Recombinant DNA vaccines: Discussion." Vaccine 8(Supplement 1): S63-S68.

Gustafsson, L., et al. (1996). "A controlled trial of a two-component acellular, a five-component acellular, and a whole-cell pertussis vaccine." The New England Journal of Medicine 334(6): 349-355.

Haj-Ahmad, Y. et al. (1986). "Development of a helper-independent human adenovirus vector and its use in the transfer of the herpes simplex virus thymidine kinase gene." J. Virol. 57(1): 267-274.

Hirano, T., et al. (2004). "Flavonoids such as Luteolin, Fisetin and Apigenin Are Inhibitors of Interleukin-4 and Interleukin-13 Production by Activated Human Basophils." International Archives of Allergy and Immunology 134(2): 135-140.

Hogan, J. S., et al. (1990). "Relationships Among Vitamin E, Selenium, and Bovine Blood Neutrophils." J. Dairy Sci. 73(9): 2372-2378.

Hogan, J. S., et al. (1992). "Bovine Neutrophil Responses to Parenteral Vitamin E." J. Dairy Sci. 75(2): 399-405.

Hogan, J. S., et al. (1993). "Vitamin E as an Adjuvant in an *Escherichia coli* J5 Vaccine." J. Dairy Sci. 76(2): 401-407.

Hsu, H.,et al. (1999) "Prospects for a hepatitis C virus vaccine." Clin. Liver Dis. 3:901-15.

http://en.wikipedia.org/wiki/Allyl_isothiocyanate, (Sep. 24, 2010.)
http://en.wikipedia.org/wild/Rubefacient, (Sep. 24, 2010).

Inoue, H., et al. (1997). "Mechanism of mustard oil-induced skin inflammation in mice." European Journal of Pharmacology 333(2-3): 231-240.

Ivanov, A. et al. (2006). "1,25—Dihydroxyvitamin D3 Enhances Systemic and Mucosal Immune Responses to Inactivated Poliovirus Vaccine in Mice." The Journal of Infectious Diseases 193(4): 598-600.

Iwarson, S. (1995). "New approaches to hepatitis A and B vaccines." APMIS 103(1-6): 321-326.

Jason, J., et al. (2002). "Vitamin A Levels and Immunity in Humans." Clin. Diagn. Lab. Immunol. 9(3): 616-621.

Jedrzejas, M. J. (2001). "Pneumococcal virulence factors: structure and function." Microbiol. Mol. Biol. Rev. 65(2): 187-207.

Jeffery, H., et al. (1993). "The preparation and characterization of poly(lactide-co-glycolide) microparticles. II. The entrapment of a model protein using a (water-in-oil)-in-water emulsion solvent evaporation technique." Pharmaceutical Research 10(3): 362-368.

Jin, Y., et al. (2006). "Separation of catechin compounds from different teas." Biotechnology Journal 1(2): 209-213.

Kalman, S., et al. (1999). "Comparative genomes of *Chlamydia pneumoniae* and *C. trachomatis*." Nature Genetics 21(4): 385.

Kang, T. H., et al. (2007). "Epigallocatechin-3-Gallate Enhances CD8+T Cell-Mediated Antitumor Immunity Induced by DNA Vaccination." Cancer Res 67(2): 802-811.

Katiyar, S. K., et al. (1999). "Prevention of UVB-induced immunosuppression in mice by the green tea polyphenol (−)-epigallocatechin-3-gallate may be associated with alterations in IL-10 and IL-12 production." Carcinogenesis 20(11): 2117-2124.

Kirk, D. D., et al. (2004). "Application of *Quillaja saponaria* extracts as oral adjuvants for plant-made vaccines." Expert Opinion on Biological Therapy 4(6): 947-958.

Kotin, R. M. (1994). "Prospects for the use of adeno-associated virus as a vector for human gene therapy." Human Gene Therapy 5:793-801.

Kurata, T., et al. (1977). "Suppressed tumor growth and metastasis by vitamin A +BCG in Lewis lung tumor bearing mice." Oncology 34(5): 212-215.

Kuroda, M., et al. (2001). "Whole genome sequencing of meticillin-resistant *Staphylococcus aureus*." Lancet 357(9264): 1225.

Lalvani, A., et al. (1997). "Rapid Effector Function in CD8+ Memory T Cells." J. Exp. Med. 186(6): 859-865.

Lebkowski, J. S., et al. (1988). "Adeno-associated virus: a vector system for efficient introduction and integration of DNA into a variety of mammalian cell types." Mol. Cell. Biol. 8(10): 3988-3996.

Lim, S.-Y., et al. (2006). "Phytol-based novel adjuvants in vaccine formulation: 1. assessment of safety and efficacy during stimulation of humoral and cell-mediated immune responses." Journal of Immune Based Therapies and Vaccines 4(1): 6-17.

Lindberg, A. A. (1999). "Glycoprotein conjugate vaccines." Vaccine 17(Supplement 2): S28-S36.

Louis, A. J., et al. (1989). "The role of substance P and calcitonin gene-related peptide in neurogenic plasma extravasation and vasodilatation in the rat." Neuroscience 32(3): pp. 581-586.

Ma, Y., et al. (2005). "The anti-tetanus immune response of neonatal mice is augmented by retinoic acid combined with polyriboinosinic:polyribocytidylic acid." Proceedings of the National Academy of Sciences of the United States of America 102(38): 13556-13561.

Mantena, S., et al. (2005). "Epigallocatechin-3-Gallate Inhibits Photocarcinogenesis Through Inhibition of Angiogenic Factors and Activation of $CD8^{^} sup +^{^}$ T Cells in Tumors." Photochemistry and Photobiology 81(5), 1174-9.

Mason, L., et al. (2004). "Systematic review of efficacy of topical rubefacients containing salicylates for the treatment of acute and chronic pain." BMJ 328(7446): 995-997.

Matsunaga, K., et al. (2001). "*Legionella pneumophila* Replication in Macrophages Inhibited by Selective Immunomodulatory Effects on Cytokine Formation by Epigallocatechin Gallate, a Major Form of Tea Catechins." Infect. Immun 69(6): 3947-3953.

McGee, J. P., et al. (2009). "The encapsulation of a model protein in poly (D, L lactide-coglycolide) microparticles of various sizes: an evaluation of process reproducibility." Journal of Microencapsulation 14(2): 197-210.

McHeyzer-Williams, M.G., et al. (1996). "Enumeration and characterization of memory cells in the TH compartment." Immunol. Rev. 50: 1-21.

McMichael, A. J., et al. (1998). "A New Look at T Cells." J. Exp. Med. 187(9): 1367-1371.

McMichael, J. C. (2000). "Vaccines for *Moraxella catarrhalis*." Vaccine 19(Supplement 1): S101-S107.

McMurray, D.N., et al. (1990). "Micronutrient status and immune function in tuberculosis." Annals of the New York Academy of Sciences 587, 59-69.

Michael, S. I., et al. (1993). "Binding-incompetent adenovirus facilitates molecular conjugate-mediated gene transfer by the receptor-mediated endocytosis pathway." Journal of Biological Chemistry 268(10): 6866-6869.

Miller, A. D. (1990). "Retrovirus Packaging Cells." Human Gene Therapy 1(1): 5-14.

Miller, A.D., et al. (1989). "Improved retroviral vectors for gene transfer and expression." Biotechniques. 7:980-990.

Miller, M., et al. (2001). "Dietary antioxidants protect gut epithelial cells from oxidant-induced apoptosis." BMC Complementary and Alternative Medicine 1(1): 11.

Mittereder, N., et al. (1994). "Evaluation of the efficacy and safety of in vitro, Adenovirus-mediated transfer of the human cystic fibrosis transmembrane conductance regulator cDNA." Human Gene Therapy 5(6): 717-729.

Muzyczka, N. Viral Expression Vectors: Current Topics in Microbiology and Immunology. New York: Springer-Verlag, 1992.97-129.

Nair, N., et al. (2002). "Grape Seed Extract Activates Th1 Cells In Vitro." Clin. Diagn. Lab. Immunol. 9(2): 470-476.

Nash, Kevin, et al. (2008) "Complete In Vitro Reconstruction of Adeno-Associated Virus DNA Replication Requires the Minichromosome Maintenance Complex" Journal of Virology 82(3):1458-1464.

Nuez, B. et al. (1993). "Bacteriophage Nf DNA region controlling late transcription: structural and functional homology with bacteriophage {varphi}29." Nucl. Acids Res. 21(12): 2861-2865.

O'Hagan, D. T., et al. (1993). "Biodegradable microparticles for oral immunization." Vaccine 11(2): 149-154.

Pizza, M., et al. (2000). "Identification of Vaccine Candidates Against Serogroup B Meningococcus by Whole-Genome Sequencing." Science 287(5459): 1816.

Prinz, W., et al. (1980). "A systematic study of the effect of vitamin C supplementation on the humoral immune response in ascorbic-dependent mamamals." Int. J. Vit. Nutr. Res. 50: 294-300.

Ramanathapuram, L. V., et al. (2006). "Vesiculated alpha-tocopheryl succinate enhances the anti-tumor effect of dendritic cell vaccines." Cancer Immunology, Immunotherapy: CII 55(2): 166-177.

Ramsay, M. E., et al. (2001). "Efficacy of meningococcal serogroup C conjugate vaccine in teenagers and toddlers in England." Lancet 357(9251): 195-6.

Rappuoli, R., et al. (1991). "Towards third-generation whooping cough vaccines." Trends in Biotechnology 9(1): 232-238.

Read, R. C., et al. (2000). "Genome sequences of *Chlamydia trachomatis* MoPn and *Chlamydia pneumoniae* AR39". Nucleic Acids Research, 28(6), 1397-1406.

Rich, D. P., et al. (1993). "Development and analysis of recombinant Adenoviruses for gene therapy of cystic fibrosis." Human Gene Therapy 4(4): 461-476.

Romanowski, et al. "Thiocyanates and Isothiocyanates, Organic" in Ullmann's Encyclopedia of Industrial Chemistry, 2000, Wiley-VCH: Weinheim.

Rosenqvist et al. (1998) Dev. Biol. Stand. 92:323-333; etc.

Ross, B. C., L. Czajkowski, et al. (2001). "Identification of vaccine candidate antigens from a genomic analysis of *Porphyromonas gingivalis*." Vaccine 19(30): 4135-4142.

Rubin, L. (2000). "Pneumococcal vaccine." Pediatric clinics of North America 47(2): 269-285.

Saurer, L., et al. (2007). "In Vitro Induction of Mucosa-Type Dendritic Cells by All-Trans Retinoic Acid." J Immunol. 179(6): 3504-3514.

Scarpa, M., et al. (1991). "Characterization of recombinant helper retroviruses from moloney-based vectors in ecotropic and amphotropic packaging cell lines." Virology 180(2): 849.

Schuchat, A. (1999). "Group B streptococcus." Lancet 353(9146): 51-56.

Schultze V., et al. (2008). "Safety of MF59™ adjuvant." Vaccine, 26 (26), 3209-3222.

Seth et al., (1994) "Mechanism of enhancement of DNA expression consequent to cointernalization of a replication-deficient adenovirus and unmodified plasmid DNA." J. Virol. 68(2): 933-940.

Shelling, A. N., et al. (1994). "Targeted integration of transfected and infected adeno-associated virus vectors containing the neomycin resistance gene." Gene Therapy 1(3): 165-169.

Shirai, et al. (2000). "Comparison of outer membrane protein genes *omp* and *pmp* in the whole genome sequences of *nChlamydia pneumoniae* isolates from Japan and the United States." J. Infect. Dis. 181(Suppl 3):5524-5527.

Sood, N. N., et al. (1985). "Epidemic dropsy following transcutaneous absorption of *Argemone mexicana* oil." Transactions of the Royal Society of Tropical Medicine and Hygiene 79(4): 510-512.

Studier, F. W., et al. (1986). "Use of bacteriophage T7 RNA polymerase to direct selective high-level expression of cloned genes." Journal of Molecular Biology 189(1): 113-130.

Sutter, R. W., et al. (2000). "Poliovirus vaccines: progress toward global poliomyelitis eradication and changing routine immunization recommendations in the United States." Pediatric clinics of North America 47(2): 287-308.

Tengerdy RP, et al. (1983) Vitamin E-enhanced humoral antibody response to *Clostridium perfringens* type D in sheep. *British Veterinary Journal* 139, 147-152.

Tengerdy, R. P. (1990). "The role of vitamin E in immune response and disease resistance." Annals of the New York Academy of Sciences 587: 24-33.

Tengerdy, R. P., et al. (1991). "Vitamin E adjuvant formulations in mice." Vaccine 9(3): 204-206.

Tengerdy, R. P., et al. (1991). "Serological responses of rams to a *Brucella ovis*—vitamin E adjuvant vaccine." Vaccine 9(4): 273-276.

Tettelin, H., et al. (2000). "Complete Genome Sequence of *Neisseria meningitidis* Serogroup B Strain MC58." Science 287(5459): 1809.

Tomasetti, et al. (2007). "Vitamin E Analogues and Immune Response in Cancer Treatment." Vitamins & Hormones 76: 463-491.

Van Der Stede, et al. (2001). "Enhanced induction of the IgA response in pigs by calcitriol after intramuscular immunization." Vaccine 19(15-16): 1870-1878.

Wagner, E., et al. (1992). "Coupling of adenovirus to transferrin-polylysine/DNA complexes greatly enhances receptor-mediated gene delivery and expression of transfected genes." Proceedings of the National Academy of Sciences of the United States of America 89(13): 6099-6103.

Wang, J., et al. (2002). "Effects of Anthocyanins and Other Phenolic Compounds on the Production of Tumor Necrosis Factor α in LPS/IFN-γ-Activated RAW 264.7 Macrophages." Journal of Agricultural and Food Chemistry 50(15): 4183-4189.

Watson, W. (2000). "Pneumococcal conjugate vaccines." The Pediatric Infectious Disease Journal 19(4): 331-332.

Wiedermann, U., et al. (1993). "Impaired mucosal antibody response to cholera toxin in vitamin A-deficient rats immunized with oral cholera vaccine." Infect. Immun 61(9): 3952-3957.

Yamamoto, Y., et al. (2004). "Protective effects of green tea catechins on alveolar macrophages against bacterial infections." Biofactors 21(1-4): 119-121.

Yu, S., et al. (2005). "All-trans retinoic acid biases immune response induced by DNA vaccine in a Th2 direction." Vaccine 23(44): 5160-5167.

Zhou, S., et al. (1994). "Adeno-associated virus 2-mediated high efficiency gene transfer into immature and mature subsets of hematopoietic progenitor cells in human umbilical cord blood." J. Exp. Med. 179(6): 1867-1875.

Zimmerman, R. K. (1999). "Poliovirus vaccine options." Am. Fam. Physician 59:113-118, 125-126.

* cited by examiner

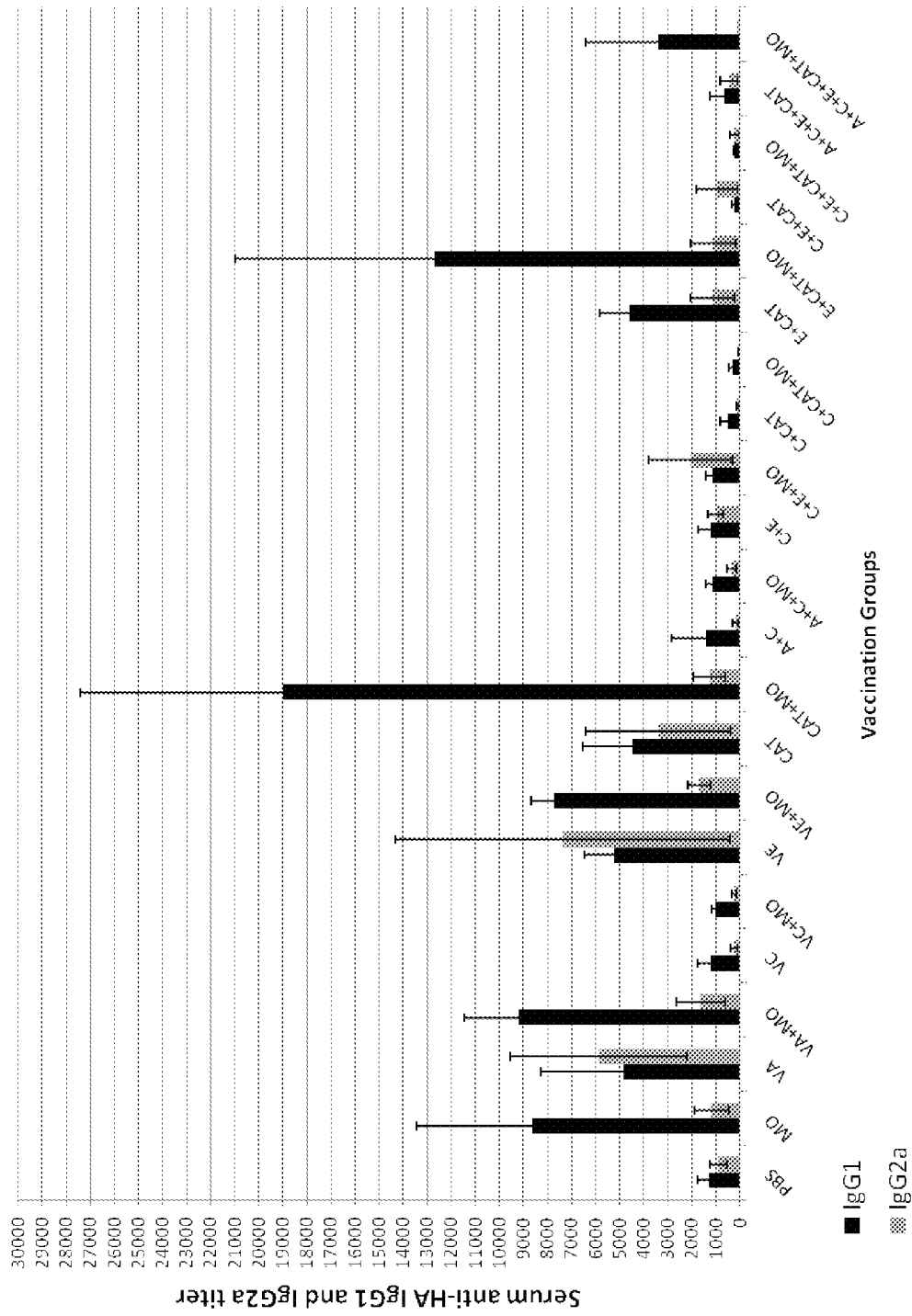

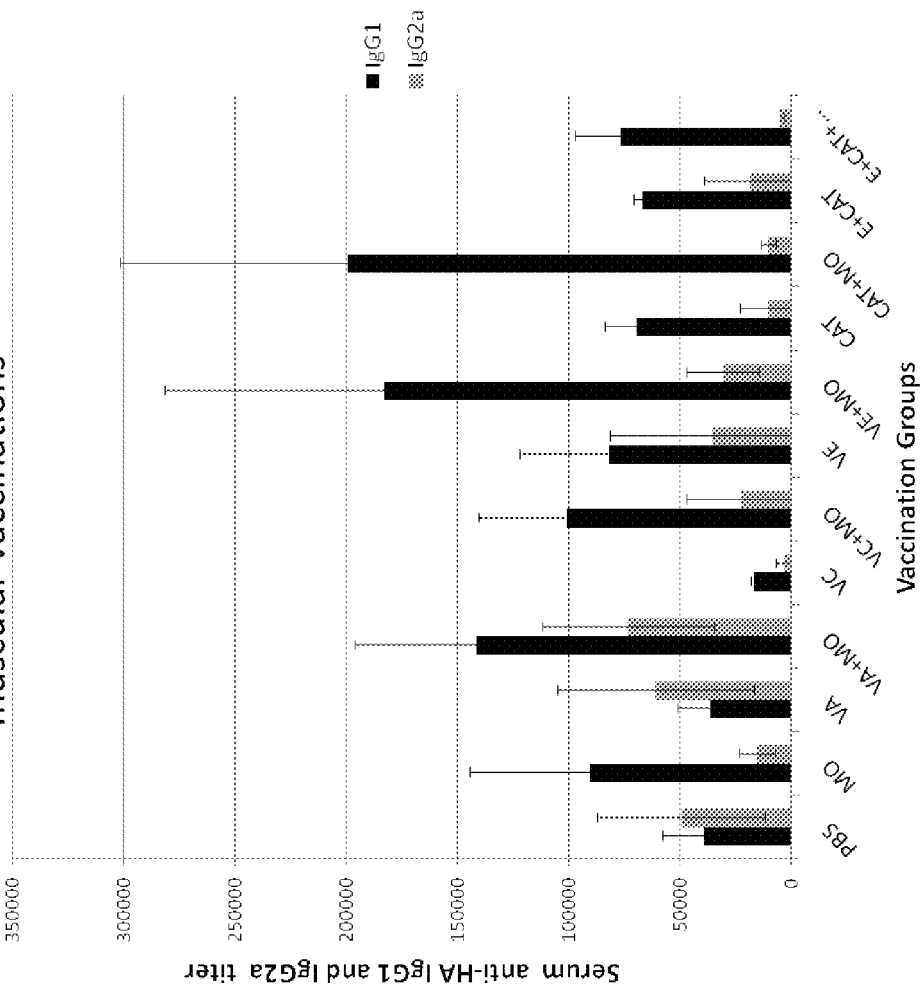

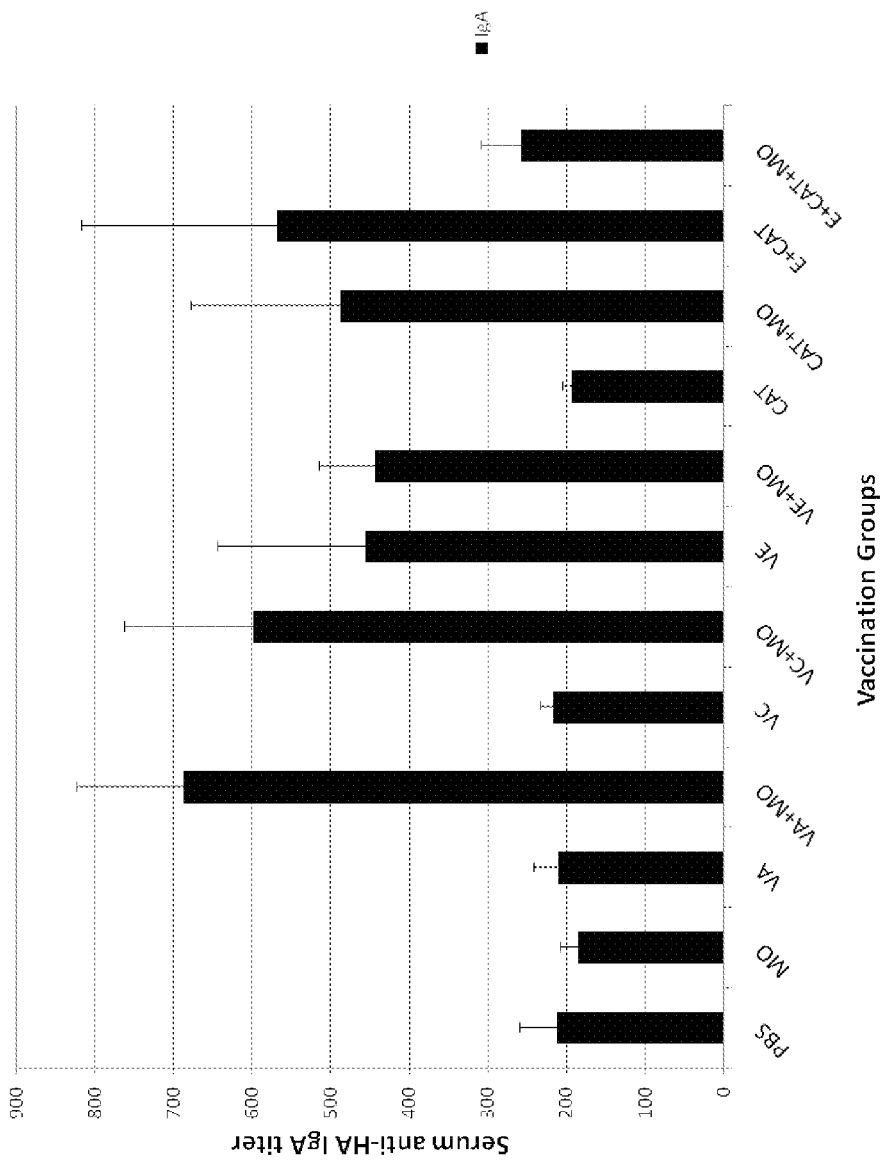

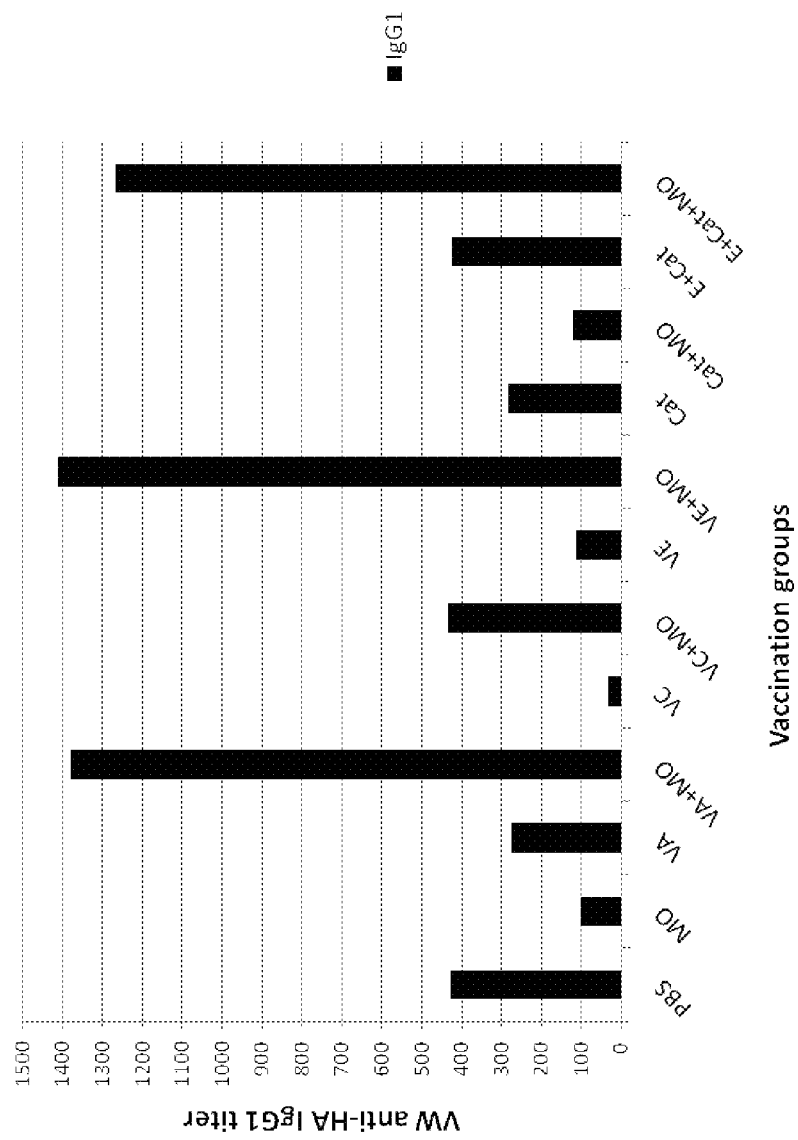
Figure 4. Vaginal Lavage anti-HA IgG1 titers at one week after two intra-muscular vaccinations

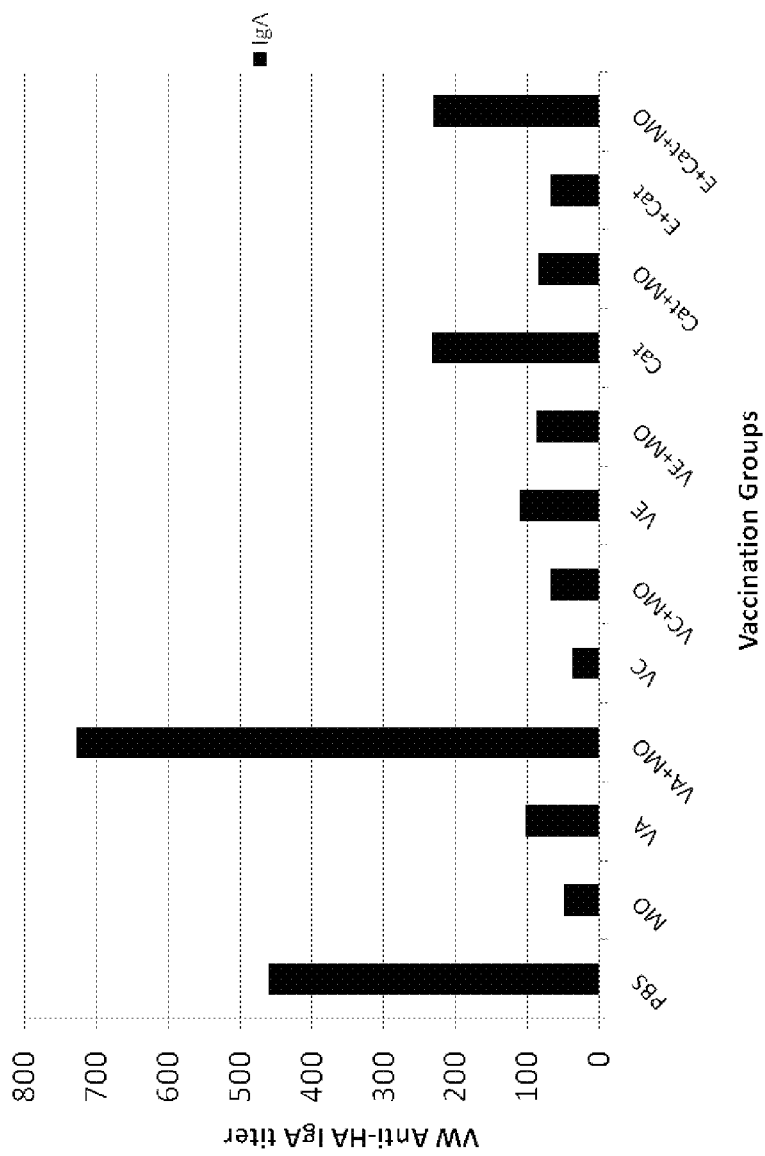

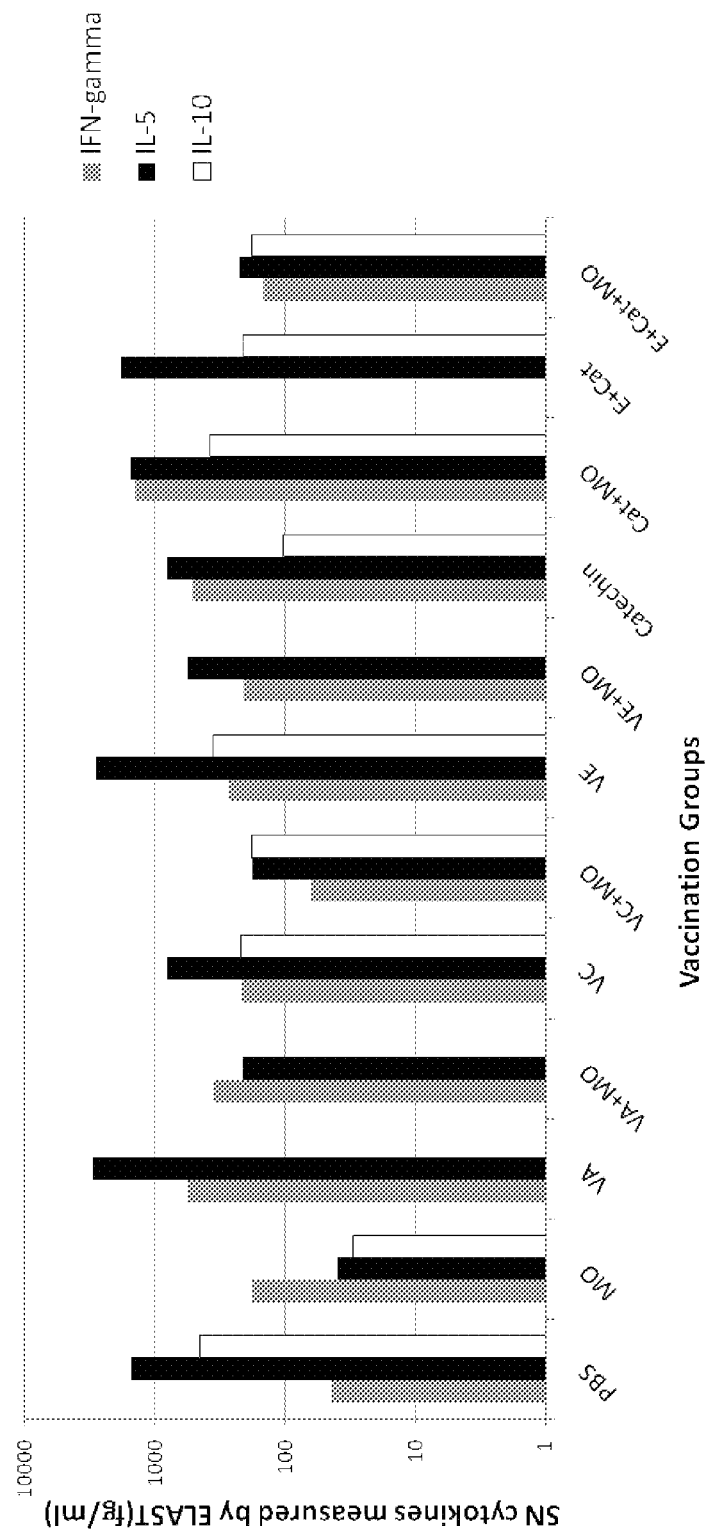

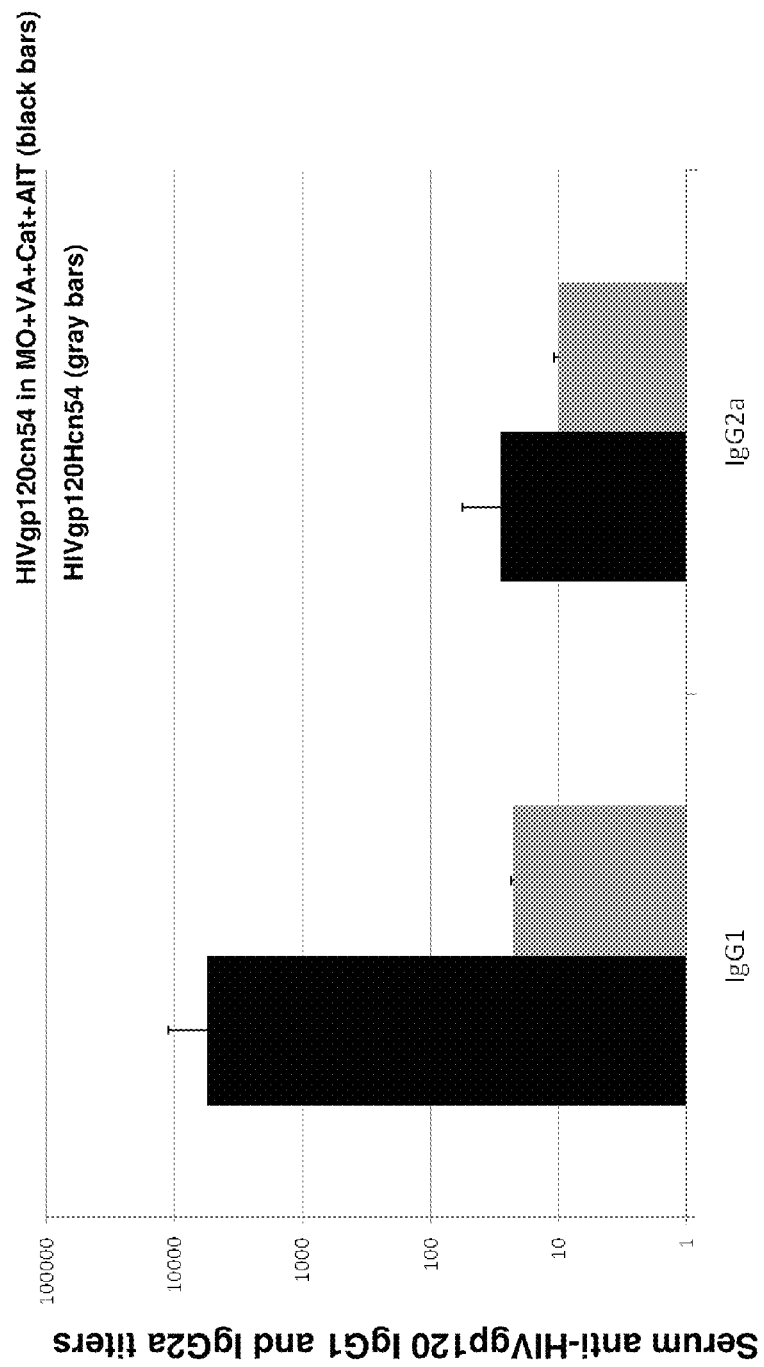
Figure 7. Serum anti-HIVgp120 IgG1 and IgG2a at two weeks following two IN vaccinations

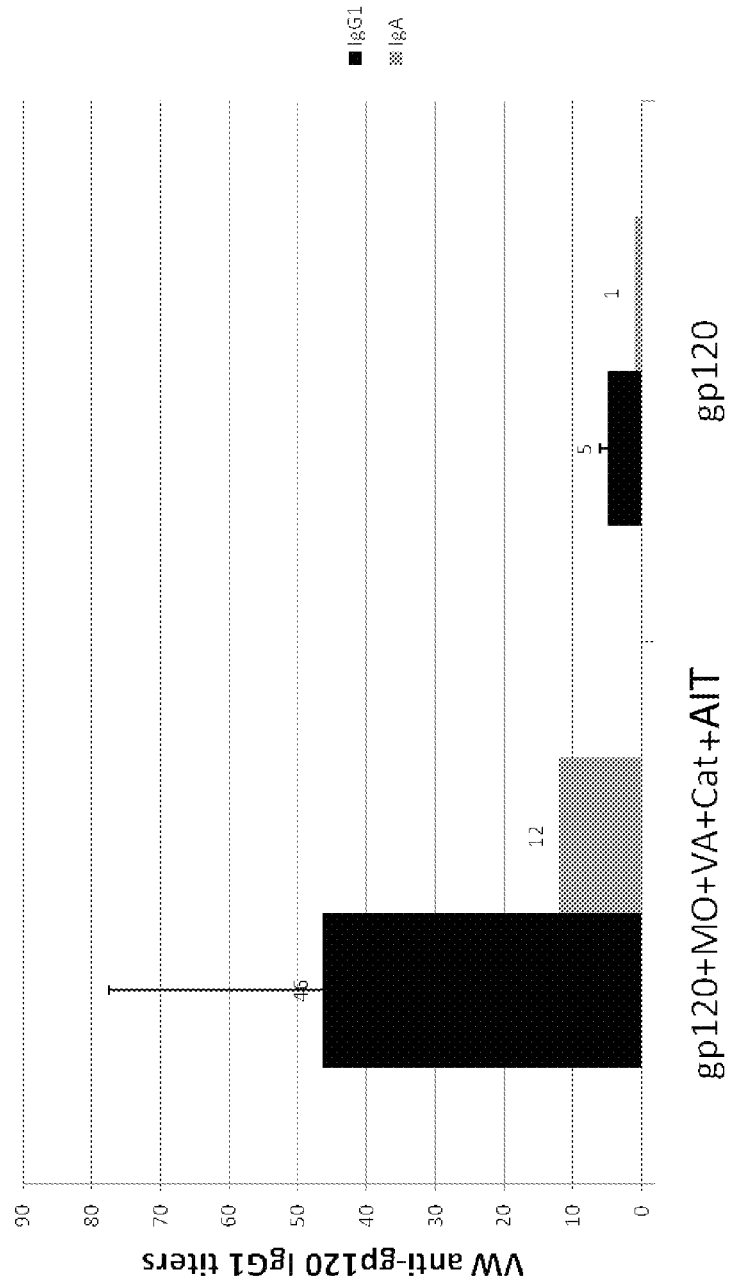
Figure 8. Vaginal Lavage anti-HIVgp120 IgG1 and IgA at two weeks following two IN/SL vaccinations

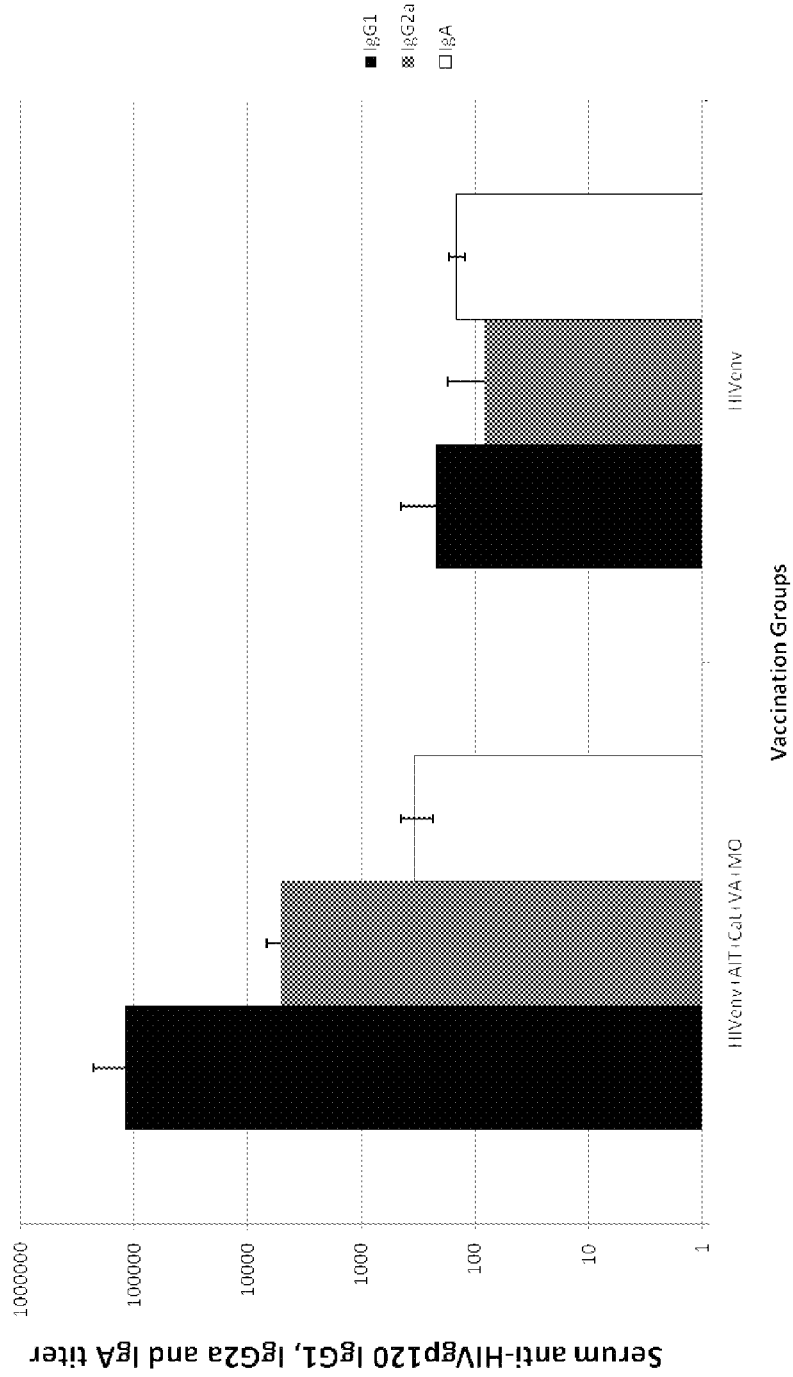
Figure 9. Serum anti-HIVgp120 IgG1, IgG2a and IgA responses at one week following two IN/SL and two IM vaccinations

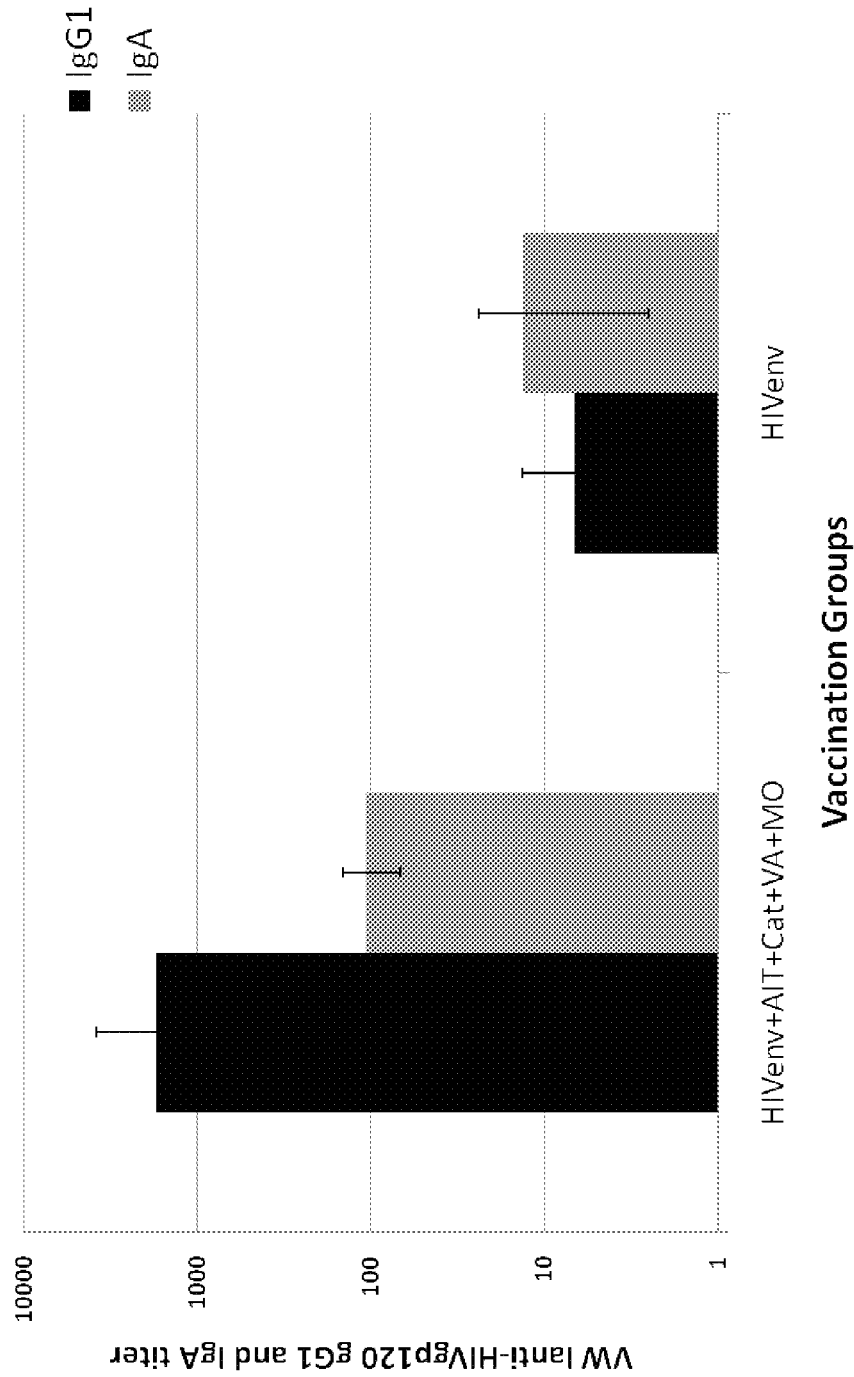

ADJUVANT COMPOSITIONS AND METHODS OF USE

CROSS REFERENCED TO RELATED APPLICATION

This application claims priority to U.S. Provisional Application No. 61/204,316 filed Jan. 5, 2009.

GOVERNMENT SUPPORT

This invention was made with government support under Grant No. 1R43AI084690-01 awarded by the National Institute of Health. The government has certain rights in this invention.

TECHNICAL FIELD

This present disclosure relates to adjuvant compositions and methods for using the same.

BACKGROUND

Vaccines are very cost effective medical interventions. However, although many diseases have been prevented through vaccinations, many others remain to be prevented. Moreover, improved vaccines are needed for a number of diseases for which vaccines already exist. A major hurdle in producing vaccines is the lack of or low immunogenicity of the vaccine. The effectiveness of a vaccine can be enhanced by using adjuvants and delivery systems. Of particular interest are adjuvants that increase the immunogenicity of a vaccine administered by a needle-free method via a mucosal route.

SUMMARY

This disclosure provides adjuvant compositions that are capable of modulating the immune response in a subject. These adjuvant compositions may also be used enhance the immunogenicity of antigens by enhancing antigen-presentation, enhancing innate immune responses through activation of, e.g., natural killer cells, and/or direct B cell activation. Also provided are methods of making the adjuvant compositions as well as methods of using the adjuvant compositions.

In certain embodiments, the compositions include mustard oil; and at least one of: (a) a flavonoid, or a flavonoid derivative, or a flavonoid derivative salt; and (b) a vitamin, or a derivative or salt thereof, where the vitamin is selected from the group consisting of vitamin A, vitamin E, vitamin D, vitamin C. In certain cases, the compositions include the mustard oil and the flavonoid, such as, a catechin, or the flavonoid derivative, or the flavonoid derivative salt. In certain cases, the flavonoid is a catechin, or a derivative or a salt thereof. In certain cases, the composition comprises the mustard oil and the vitamin, or a derivative or salt thereof. In certain embodiments, the composition includes mustard oil, the flavonoid, or the flavonoid derivative, or the flavonoid derivative salt and the vitamin, or a derivative or salt thereof. In certain embodiments, the composition includes the mustard oil and the vitamin may be vitamin E, or a derivative or salt thereof. In certain embodiments, the composition includes the mustard oil and vitamin A, or a derivative or salt thereof. In certain embodiments, the composition includes the mustard oil and vitamin C, or a derivative or salt thereof. In certain embodiments, the composition includes the mustard oil, a catechin, or a derivative or salt thereof, and vitamin A, or a derivative or a salt thereof. In certain embodiments, the composition includes the mustard oil, a catechin, or a derivative or salt thereof, and vitamin E, or a derivative or a salt thereof. In certain embodiments, the composition includes the mustard oil, the flavonoid, such as a catechin, or the flavonoid derivative, or the flavonoid derivative salt, and allyl isothiocyanate. In certain embodiments, the composition includes the mustard oil, the vitamin, such as vitamin A, or a derivative or salt thereof, and allyl isothiocyanate. In certain embodiments, the composition includes the mustard oil, the flavonoid, such as catechin, or the flavonoid derivative, or the flavonoid derivative salt, the vitamin, such as vitamin A, or a derivative or salt thereof, and allyl isothiocyanate. In certain aspects, the composition further includes an antigen. In certain embodiments, the adjuvant compositions include allyl isothiocyanate and at least one of: a flavonoid and a vitamin.

The compositions may be administered to a subject, such as a mammal, by a number of routes, such as, intranasal, pulmonary, sublingual, oral, buccal, intra-vaginal, intra-rectal, ocular, intradermal, transdermal, transcuataneous, subcutaneous, intra-venous and intramuscular.

Also provided are methods for making the compositions, the method includes admixing of the mustard oil and at least one of the flavonoid, or the flavonoid derivative, or the flavonoid derivative salt; and the vitamin, or derivative or salt thereof.

Also provided herein are compositions that include a pharmaceutically acceptable vegetable oil; a flavonoid, or a flavonoid derivative, or a flavonoid derivative salt; and a vitamin, or a vitamin derivative, or a vitamin derivative salt, where the vitamin is selected from the group consisting of vitamin A, vitamin E, vitamin D, vitamin C. In certain cases, the compositions include the vegetable oil and the flavonoid, such as, a catechin, or the flavonoid derivative, or the flavonoid derivative salt. In certain cases, the flavonoid is a catechin, or a derivative or a salt thereof. In certain cases, the composition comprises the vegetable oil and the vitamin, or a derivative or salt thereof. In certain embodiments, the composition includes vegetable oil, the flavonoid, or the flavonoid derivative, or the flavonoid derivative salt and the vitamin, or a derivative or salt thereof. In certain embodiments, the composition includes the vegetable oil and the vitamin may be vitamin E, or a derivative or salt thereof. In certain embodiments, the composition includes the vegetable oil and vitamin A, or a derivative or salt thereof. In certain embodiments, the composition includes the vegetable oil and vitamin C, or a derivative or salt thereof. In certain embodiments, the composition includes the vegetable oil, a catechin, or a derivative or salt thereof, and vitamin A, or a derivative or a salt thereof. In certain embodiments, the composition includes the vegetable oil, a catechin, or a derivative or salt thereof, and vitamin E, or a derivative or a salt thereof. In certain embodiments, the composition includes the vegetable oil, the flavonoid, such as a catechin, or the flavonoid derivative, or the flavonoid derivative salt, and allyl isothiocyanate. In certain embodiments, the composition includes the vegetable oil, the vitamin, such as vitamin A, or a derivative or salt thereof, and allyl isothiocyanate. In certain embodiments, the composition includes the vegetable oil, the flavonoid, such as catechin, or the flavonoid derivative, or the flavonoid derivative salt, the vitamin, such as vitamin A, or a derivative or salt thereof, and allyl isothiocyanate. In certain aspects, the composition further includes an antigen.

BRIEF DESCRIPTION OF THE DRAWINGS

FIG. 1 shows serum titers of anti-HA IgG1 antibody and anti-influenza-HA IgG2a antibody at three-weeks after single intramuscular (IM) vaccination.

FIG. 2 shows serum titers of anti-influenza-HA IgG1 antibody and anti-HA IgG2a antibody at one-week after the second intramuscular (IM) vaccination.

FIG. 3 shows serum titers of anti-influenza-HA IgA antibody at one-week after the second intramuscular (IM) vaccination.

FIG. 4 shows titers of anti-influenza-HA IgG1 antibody in vaginal lavage at one-week after the second intramuscular (IM) vaccination.

FIG. 5 shows titers of anti-influenza-HA IgA antibody in vaginal lavage at one-week after the second intramuscular (IM) vaccination.

FIG. 6 shows TH1, TH2 and Treg responses following ex vivo activation with influenza-HA at one-week after the second intramuscular (IM) vaccination.

FIG. 7 shows serum titers of anti-HIVgp120 IgG1 antibody and anti-HIVgp-120 IgG2a antibody at two weeks after the second intranasal (IN) vaccination.

FIG. 8 shows titers of anti-HIVgp120 IgG1 antibody and anti-HIVgp120 IgA antibody in vaginal lavage at two weeks after the second IN vaccination.

FIG. 9 shows serum titers of anti-HIVgp120 IgG1, IgG2a, and IgA antibodies at one week after two IN/SL (Intranasal/sublingual) and two IM vaccinations.

FIG. 10 shows titers of anti-HIVgp120 IgG1 and IgA antibodies in vaginal lavage at one week after two IN/SL (Intranasal/sublingual) and two IM vaccinations.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. To the extent such publications may set out definitions of a term that conflicts with the explicit or implicit definition of the present disclosure, the definition of the present disclosure controls.

It must be noted that as used herein and in the appended claims, the singular forms "a", "an", and "the" include plural referents unless the context clearly dictates otherwise. Thus, for example, reference to "an adjuvant composition" includes a plurality of adjuvant composition, reference to "a vitamin" includes one, two, or more vitamins, and reference to "a flavonoid" includes one, two, or more flavonoids, and so forth. The terms adjuvant and delivery system may be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

The present disclosure provides adjuvant compositions that are capable of modulating the immune response in a subject. These adjuvant compositions may also be used enhance the immunogenicity of antigens by enhancing antigen-presentation, enhancing innate immune responses through activation of, e.g., natural killer cells, and/or direct B cell activation. Also provided are methods of making the adjuvant compositions as well as methods of using the adjuvant compositions.

Definitions

The phrases "adjuvant composition(s)" refer to a composition that when administered to a subject is capable of inducing an immune response in the subject. When administered in combination with an antigen, the "adjuvant compositions" are capable of eliciting an antigen-specific immune response.

An "immune response" to an antigen or composition is the development in a subject of a humoral and/or a cellular immune response to molecules present in the antigen or composition of interest. A "humoral immune response" refers to an immune response mediated primarily by antibody molecules, while a "cellular immune response" is one mediated primarily by T-lymphocytes and/or other white blood cells.

The phrase "pharmaceutically acceptable" refers to substance that is generally safe and is acceptable for veterinary use when the subject is a non-human. "Pharmaceutically acceptable" for humans refers to substance that is generally safe and is acceptable for human pharmaceutical use.

The term "antigen" refers to any substance that can be recognized by the immune system (e.g., bound by an antibody or processed so as to elicit a cellular immune response by, e.g. T cells) under appropriate conditions. An antigen contains one or more epitopes. A B-cell epitope includes at least about 3-5 amino acids, for example, 4 or more amino acids. A hapten or a polysaccharide may also serve as a B cell epitope. A T-cell epitope, such as a cytotoxic T-cell (CTL) epitope, may include at least about 7-9 amino acids, for example, 8 or more amino acids. A helper T-cell epitope may include at least about 12-20 amino acids. The term "antigen" denotes both subunit antigens (i.e., antigens which are separate from the whole organism with which the antigen is associated in nature), as well as, killed, attenuated or inactivated bacteria, viruses, fungi, parasites or other microbes, prions, allergens or any other disease causing agents. An antigen may be a modified protein that includes modifications, such as deletions, additions and substitutions (generally conservative in nature) to the native protein sequence. The term antigen also denotes nucleic acids (DNA or RNA) encoding a protein or peptide antigen.

"Penetration enhancement" or "permeation enhancement" as used herein refers to increasing the permeability of skin or mucosa to an antigen so as to increase the rate at which the antigen passes through the skin or mucosa and enters the lymph node or the blood stream.

A "therapeutically effective amount" or "efficacious amount" means the amount of a compound that, when administered to a mammal or other subject for preventing or treating a disease, is sufficient to affect such prevention or treatment for the disease. The "therapeutically effective amount" will vary depending on the compound, the disease and its severity and the age, weight, etc., of the subject to be treated.

Overview

This disclosure provides adjuvant compositions that are capable of inducing an immune response. These adjuvant compositions may also be used enhance the immunogenicity of antigens by enhancing antigen-presentation, enhancing innate immune responses through activation of, e.g. natural killer cells, and/or by direct B cell activation. Also provided are methods of making the adjuvant compositions as well as methods of using the adjuvant compositions.

Adjuvant Compositions

Adjuvant compositions provided herein include: a pharmaceutically acceptable vegetable oil; a flavonoid, or a flavonoid derivative, or a flavonoid derivative salt; and a vitamin, or a derivative, or a salt thereof. The vitamin may be vitamin A, vitamin E, vitamin D, vitamin C.

In another embodiment, the compositions provided herein include: mustard oil with or without allyl isothiocyanate (essential oil of mustard); and at least one of: (a) a flavonoid, or a flavonoid derivative, or a flavonoid derivative salt; and (b) a vitamin, or a derivative, or a salt thereof. The vitamin may be vitamin A, vitamin E, vitamin D, vitamin C, or a derivative or a salt thereof.

In certain embodiments, the flavonoid is a flavone, a flavonol, a flavonone, a catechin, anthocyanid, or isoflavone, or derivatives thereof, or salts of the derivatives. In certain embodiments, the adjuvant composition includes mustard oil and a catechin, such as, catechin hydrate.

In certain embodiments, the adjuvant compositions include one or more vitamins, such as, Vitamin A, Vitamin E, Vitamin D, Vitamin C, derivatives, and salts thereof and a vegetable oil carrier, such as mustard oil. The adjuvant compositions may optionally include a flavonoid or a flavonoid derivative or salt of the flavonoid derivative. In certain embodiments, the adjuvant compositions include Vitamin A and an oil carrier, such as, mustard oil. In certain embodiments, the adjuvant compositions include Vitamin E and an oil carrier, such as, mustard oil.

The adjuvant compositions may additionally include other additives, such as preservatives, colorants, flavorants, etc. The adjuvant compositions may additionally include an antigen.

Pharmaceutically Acceptable Vegetable Oil Carriers

A "pharmaceutically acceptable vegetable oil carrier" as used herein refers to a vegetable oil that is suitable for administration to a human or non-human animal by a desirable route, e.g., systemic or mucosal route, including oral and topical routes of delivery. Edible adjuvant compositions are contemplated by the present disclosure.

"Vegetable oil" refers to oil obtainable from a plant or a plant product, and encompasses oil obtainable from seeds (including nuts, grains), fruits, roots, flowers, stems, etc. Examples include corn oil, mustard oil, olive oil, coconut oil, safflower oil, soybean oil, and the like. Vegetable oils of the present disclosure encompass oils obtainable from non-genetically modified and from genetically modified plants. Vegetable oils encompass vegetable oils having properties of a rubefacient, i.e., oils that promotes dilation of capillaries and an increase in blood circulation, e.g., when applied topically to skin. Vegetable oil may be derived from a plant or plant product (e.g., a non-genetically modified or genetically modified plant or plant product), or may be produced synthetically, e.g., by mixing the individual components found in vegetable oils, where the individual components may be derived from plants or plant products, or produced synthetically. The plants which provide the source for the vegetable oil or the individual fatty acids may be genetically modified.

In certain embodiments, the vegetable oil is a mustard oil. "Mustard oil" as used herein refers to oil that is obtainable from seeds of a mustard plant of *Brassicacae*, where the oil is obtainable from the mustard plant without application of heat during extraction (e.g., free mustard oil obtainable by a cold-press extraction method). Mustard oil obtainable from seeds of a mustard plant without application of heat have a lower amounts of (e.g., no significant or detectable) allyl isothiocyanate than oil that may be obtainable from the same seeds using a heat-based extraction method (e.g., by application of steam). Mustard plants of Brassicacae from which mustard oils useful as carriers in the compositions of the present disclosure may be obtainable include, but are not necessarily limited to, *Brassica rapa* (edible greens), *Brassica nigra* (black mustard), *Brassica juncea* (brown mustard), *Brassica hirta* (white or yellow mustard), *Brassica carinata* (Ethiopian mustard), *Brassica oleracea* (wild mustard), *Brassica campestris* (including *Brassica napus* L. and *B. campestris* L.), and *Brassica napus*. Oils contemplated by "mustard oil" can include oil obtainable from rapeseed.

In certain embodiments, the vegetable oil is canola oil. Such canola oil may have the following composition: 6-8% Saturated Fatty Acids (with 3.5 Palmitic Acid); 14.4% Monounstaurated Fatty Acids (with 60% Oleic Acid); and 69.3% Polyunsaturated Fatty Acids (with 20% Linoleic Acid, 10% Alpha Linolenic Acid).

In certain embodiments, the vegetable oil used in the compositions described herein may be composed of about 14%-70% monounsaturated fatty acids, about 18%-22% polyunsaturated fatty acids and about 5%-12% saturated fatty acids. The monounsaturated fatty acids may have about 18%-51% erucic acid and about 7%-22% oleic acid, the polyunsaturated fatty acids may have about 9-15% linolenic acid and about 6-24% linoleic acid, and the saturated fatty acids may have about 3-4% palmitic acid.

In certain embodiments, the vegetable oil used in the compositions described herein may be composed of 14%-70% monounsaturated fatty acids, 18%-22% polyunsaturated fatty acids and 5%-12% saturated fatty acids.

In certain embodiments, the vegetable oil used in the compositions described herein may be composed of 14%-20% monounsaturated fatty acids, 18%-20% polyunsaturated fatty acids and 5%-6% saturated fatty acids.

In certain embodiments, the vegetable oil used in the compositions described herein may be composed of about 60%-70% monounsaturated fatty acids, about 18%-22% polyunsaturated fatty acids and about 5%-6% saturated fatty acids.

Where the vegetable oil is a mustard oil, in certain embodiments, the mustard oil may have the following composition: monounsaturated fatty acids (erucic acid (18-51%), oleic acid (7-22%)), polyunsaturated fatty acids (linolenic (9-15%) and linoleic (6-24%)), and 5% saturated fatty acids. The mustard oil may additionally also include other components, such as, proteins (30%), phenolics, phytin and dithiol thiones. Mustard oil may also contain 490 mg/100 gm of calcium. Mustard oil may also contain 9-15% omega 3 fatty acids.

In some embodiments, the mustard oil is one obtainable from *Brassica rapa*. Mustard oil obtainable from *Brassica rapa* includes an oil having the following composition: 5.4% Saturated Fatty Acids (with 2.7% Palmitic Acid, 1.0% Stearic Acid, 0.6% Behenic, 1.1% Other); 67.3% Monounstaurated Fatty Acids (with 23.3% Oleic, 10.0% Gadoleic, 33.8% Erucic); and 20.6% Polyunsaturated Fatty Acids (with 9.4% Linoleic Acid, 9.9% Alpha Linolenic Acid).

In certain embodiments, the vegetable oil carrier (e.g., mustard oil) may be a mixture of one or more vegetable oils, for example, mustard oil (with or without added AIT) and corn oil; mustard oil (with or without added AIT) and soy bean oil; mustard oil (with or without AIT) and coconut oil. The present disclosure also contemplates compositions having a vegetable oil carrier that itself is a rubifacient and/or combined with a rubefacient oil. Examples of rubefacient oils include Oil of Wintergreen (Methyl Salicylate), mustard oil, and Rosemary oil (*Rosmarinus officinalis*).

Flavonoids

The adjuvant compositions may include one or more flavonoids or derivates or salts thereof. Flavonoids (also known as bioflavonoids) are phytochemicals found in fruits and vegetables. Flavonoids are of the following types: Flavones (e.g., apigenin, luteolin), Flavonols (e.g., quercetin, myricetin), Flavanones (e.g., naringenin, hesperidin), Catechins (e.g., epicatechin, catechin, epigallocatechin, gallocatechin, epicatechin gallate and epigallocatechin gallate), Anthocyanidins/anthocyanins (e.g., cyanidin, pelargonidin), and Isoflavones (e.g., genistein, daidzein).

In certain embodiments, the adjuvant compositions may include epigallocatechin gallate (EGCG), a form of catechin (polyphenols). In some embodiments, the adjuvant compositions may include a catechin, such as, catechin hydrate. In some embodiments, the catechin is not a multimeric form of catechin.

Vitamins

The adjuvant compositions may optionally include one or more vitamins, or derivatives or salts thereof. The one or more vitamins may be one or more of vitamin A, vitamin E, vitamin D, vitamin C, and derivatives and salts thereof.

Vitamin A.

Vitamin A is a fat-soluble vitamin that is derived from two sources: preformed retinoids and provitamin carotenoids. Retinoids, such as retinal and retinoic acid, are found in animal sources like liver, kidney, eggs, and dairy produce. Carotenoids like beta-carotene (which has the highest vitamin A activity) are found in plants such as dark or yellow vegetables and carrots. Vitamin A is also known as retinol, retinoic acid, Axerophthol, Vitamin A alcohol, Vitamin A1, all-trans-3,7-Dimethyl-9-(2,6,6-trimethyl-1-cyclohexen-1-yl)-2,4,6,8-nonatetraen-1-ol. In certain cases, an acid derivation of Vitamin A, all-trans retinoic acid (ATRA), may be included in the adjuvant compositions. In certain cases, the adjuvant compositions may include retinoids, for example, isotretinoin (Ro 4-3780), etretinate (RO 10-9359; a synthetic retinoid), or motretinide (Ro 11-1430). In certain cases, vitamin A palmitate (VA) may be included in the adjuvant compositions.

Vitamin E.

Of the eight natural substances exerting vitamin E activity ($\alpha$-, $\beta$-, $\delta$-, and $\gamma$-tocopherols and $\alpha$-, $\beta$-, $\delta$-, and $\gamma$-tocotrienols), $\alpha$-tocopherol ($\alpha$-T) has traditionally been regarded as the most important vitamin because it exerts the highest biological activity of all vitamins when assessed in animal model systems. Vitamin E is also synonymous with ($\pm$)-$\alpha$-Tocopherol and DL-all-rac-$\alpha$-Tocopherol, 5,7,8-Trimethyltocol, D-$\alpha$-Tocopherol, 2,5,7,8-Tetramethyl-2-(4',8',12'-trimethyltridecyl)-6-chromanol, and a non-oxidizing version (+)-$\alpha$-Tocopherol acetate and the related all-rac-$\alpha$-Tocopheryl acetate. A related molecule is D-$\alpha$-Tocopherol succinate, Vitamin E succinate.

In certain embodiments, the vitamin E included in the adjuvant compositions may be $\alpha$-tocopherol ($\alpha$-T). In other cases, a vitamin E analog, such as Alpha tocopheryl succinate (alpha-TOS) may be included in the adjuvant compositions.

Vitamin D.

Vitamin D is a group of fat-soluble prohormones, the two major forms of which are vitamin $D_2$ (or ergocalciferol) and vitamin $D_3$ (or cholecalciferol). Vitamin D obtained from sun exposure, food, and supplements, is biologically inert and must undergo two hydroxylation reactions to be activated in the body. Calcitriol (1,25-Dihydroxycholecalciferol) is the active form of vitamin D found in the body. The term vitamin D refers to these metabolites and other analogues of these substances. In certain embodiments, the adjuvant compositions may include 1,25-Dihydroxyvitamin $D_3$ ($DHVD_3$).

Vitamin C.

Vitamin C or L-ascorbic acid is an essential nutrient for humans. Ascorbate (an ion of ascorbic acid) is required for a range of essential metabolic reactions in all animals and plants. The pharmacophore of vitamin C is the ascorbate ion. In living organisms, ascorbate is an anti-oxidant, since it protects the body against oxidative stress, and is a cofactor in several vital enzymatic reactions. Vitamin C is purely the L-enantiomer of ascorbate; the opposite D-enantiomer has no physiological significance.

Additives

In certain embodiments, the vegetable oil carrier of the adjuvant composition may include allyl isothiocyanate (AIT). Allyl isothiocyanate (AIT) is also referred to as volatile oil of mustard or essential oil of mustard or oil of mustard. AIT is an organosulfur compound of the formula $CH_2CHCH_2NCS$. AIT is responsible for the pungent taste of mustard, horseradish, and wasabi. It is slightly soluble in water, but well soluble in most organic solvents. Allyl isothiocyanate comes from the seeds of black or brown Indian mustard. When these mustard seeds are broken, the enzyme myrosinase is released and acts on a glucosinolate known as sinigrin to give allyl isothiocyanate. Allyl isothiocyanate serves the plant as a defense against herbivores; since it is harmful to the plant itself, it is stored in the harmless form of the glucosinolate, separate from the myrosinase enzyme. When an animal chews the plant, the allyl isothiocyanate is released, repelling the animal. Allyl isothiocyanate is produced commercially by the reaction of allyl chloride and potassium thiocyanate: $CH_2$=$CHCH_2Cl$+ $KSCN \rightarrow CH_2$=$CHCH_2NCS$+$KCl$. The product obtained in this fashion is sometimes known as synthetic mustard oil. Allyl isothiocyanate can also be liberated by dry distillation of the seeds. The product obtained in this fashion is known as volatile oil of mustard and is usually around 92% pure. It is used principally as a flavoring agent in foods. Synthetic allyl isothiocyanate is used as an insecticide, bacterialcide, and nematocide, and is used in certain cases for crop protection.

In certain cases, the adjuvant composition may be composed of: AIT and a vitamin (such as, one or more of the vitamins A, C, D, E, or salts or derivatives thereof). In certain cases, the adjuvant composition may be composed of: AIT and a flavonoid (such as a catechin, for example, catechin hydrate). In certain cases, the adjuvant composition may be composed of: AIT, a vitamin (such as, one or more of the vitamins A, C, D, E, or salts or derivatives thereof), and a flavonoid (such as a catechin, for example, catechin hydrate).

The adjuvant compositions may include MF59 that contains squalene, a terpenoid plant derivative which has been shown adjuvant properties in animal and human studies. However, in certain embodiments MF59 or squalene may not be included in the adjuvant compositions. Thus, in some embodiments, the adjuvant compositions provided herein include a flavonoid; a pharmaceutically acceptable oil carrier; and optionally one or more vitamins selected from the group consisting of Vitamin A, Vitamin E and Vitamin C but does not include MF59 or squalene.

The adjuvant compositions may include saponin and its derivative QS-21. However, in certain embodiments saponin may not be included in the adjuvant compositions. Thus, in some embodiments, the adjuvant compositions provided herein include a flavonoid; a pharmaceutically acceptable oil carrier; and optionally one or more vitamins selected from the group consisting of Vitamin A, Vitamin E and Vitamin C but does not include saponin or its derivatives.

Derivatives of phytol, a dietary diterpene alcohol, similar in structure to naturally occurring isoprenoid adjuvants, elicit increased titers of all major IgG subclasses, especially IgG2a and cytotoxic effector T cell responses. The adjuvant compositions may include phytol or its derivates. However, in certain embodiments phytol may not be included in the adjuvant compositions. Thus, in some embodiments, the adjuvant compositions provided herein include a flavonoid; an oil carrier; and optionally one or more vitamins selected from the group consisting of Vitamin A, Vitamin E and Vitamin C but does not include phytol or its derivatives.

The adjuvant compositions may include other additives, such as, gelatin, antibiotics, sorbitol, sucrose, lactose, other sugars, bioadhesives, mucoadhesives (e.g., hyaluronic acid or a derivatie thereof, for example, HYAFF), hydrophilic polymers and hydrogels, polyethylene oxide homopolymers, chitosan, Beeswax, and the like.

The adjuvant compositions may include immunogenicity enhancing agents, such as, lipopolysaccharides, enterotoxins such as the heat labile toxin from *Escherichia coli* bacterium, cholera toxin from *Vibrio cholerae*, toll like receptor agonists (e.g., CpG or CpG oligonucleotides). The adjuvant compositions may be combined with other vaccine delivery systems, such as, alum, liposomes, oil-in-water emulsions, for example.

The adjuvant compositions may be formulated with large, slowly metabolized macromolecules such as proteins, polysaccharides, polylactic acids, polyglycolic acids, polymeric amino acids, amino acid copolymers, and inactive virus particles. Examples of particulate carriers include those derived from polymethyl methacrylate polymers, as well as microparticles derived from poly(lactides) and poly(lactide co glycolides), known as PLG.

The adjuvant compositions may include The mutant forms of a holotoxin, e.g. from *E. coli*, comprising the mutated A subunit and the B subunit, which may be oligomeric, as in the wild-type holotoxin. The B subunit is preferably not mutated. However, it is envisaged that a mutated A subunit may be used in isolation from the B subunit, either in an essentially pure form or complexed with other agents, which may replace the B subunit and/or its functional contribution. LT mutants for use in the compositions include mutants with one or more of the following mutations: a mutation in the A subunit of the serine at position 63, and a mutation in the A subunit of the alanine at position 72, for example, the serine at position 63 is replaced with a lysine and the alanine at position 72 is replaced with arginine.

The adjuvant compositions may include may include cholera toxin ("CT") or detoxified mutants thereof and microparticles (i.e., a particle of about 100 nm to about 150 μm in diameter, more preferably about 200 nm to about 30 μm in diameter, and still more preferably about 500 nm to about 10 μm in diameter) formed from materials that are biodegradable and non-toxic (e.g., a poly(.alpha.-hydroxy acid), a polyhydroxybutyric acid, a polyorthoester, a polyanhydride, a polycaprolactone, etc.).

The adjuvant compositions disclosed herein may be formulated as microparticle using a poly(α-hydroxy acid), in particular, from a poly(lactide) ("PLA"), a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered antigen. If the composition includes an antigen, the antigen may be entrapped within the microparticles, or may be adsorbed onto their surface.

In certain embodiments, the compositions disclosed herein include, an immuno-modulatory factor, for example, a protein that is capable of modulating an immune response. Non-limiting examples of immunomodulatory factors include lymphokines (also known as cytokines), such as IL-6, TGF-beta, IL-1, IL-2, IL-3, etc.); and chemokines (e.g., secreted proteins such as macrophage inhibiting factor). Certain cytokines, for example TRANCE, flt-3L, and a secreted form of CD40L are capable of enhancing the immunostimulatory capacity of APCs. Non-limiting examples of cytokines which may be used alone or in combination in the compositions disclosed herein include, interleukin-2 (IL-2), stem cell factor (SCF), interleukin 3 (IL-3), interleukin 6 (IL-6), interleukin 12 (IL-12), G-CSF, granulocyte macropliage-colony stimulating factor (GM-CSF), interleukin-1 alpha (IL-1.alpha.), interleukin-11 (IL-11), MIP-1.gamma., leukemia inhibitory factor (LIF), c-kit ligand, thrombopoietin (TPO), CD40 ligand (CD40L), tumor necrosis factor-related activation-induced cytokine (TRANCE) and flt3 ligand (flt-3L).

The adjuvant compositions may include emulsifiers, such as, lecithin, for example phospholipids and/or surfactants that are amphiphilic and acceptable for human and/or veterinary use. The surfactants may be ionic (e.g. Tween 80), cationic (e.g. CTAB) or zwitterionic (e.g. CHAPS). The acceptability of a surfactant for human and/or veterinary use may be determined by those of skill in the art. A surfactant is amphiphilic if a part of the surfactant molecule is hydrophobic and a part is hydrophilic. Examples of surfactants useful in the adjuvant compositions disclosed herein include, but are not limited to, a Tween surfactant and a Span surfactant. Tween and Span surfactants include, but are not limited to, monolaureate (Tween 20, Tween 21, Span 20), monopalmitate (Tween 40, Span 40), monostearate (Tween 60, Tween 61, Span 60), tristearate (Tween 65, Span 65), monooleate (Tween 80, Tween 81, Span 80) and trioleate (Tween 85, Span 85).

The adjuvant compositions may include pharmaceutically acceptable auxiliary substances as required to approximate physiological conditions such as pH adjusting and buffering agents, and the like, for example, sodium acetate, sodium chloride, potassium chloride, calcium chloride, sodium lactate, phosphate buffer saline, and the like.

The adjuvant compositions may include medicinal rubefacients, such as, Capsaicin (derived from Cayenne, *Capsicum minimum*), Salicylates (such as Oil of Wintergreen, Methyl Salicylate), Nicotinate esters, Rubbing alcohol, common herbal rubefacients include: Cloves (*Eugenia caryphyllus*), Garlic (*Allium sativum*), Ginger (*Zingiber officinale*), Horseradish (*Cochlearia armoracia*), Mustard (e.g., *Brassica alba* or *B. nigra*), Nettle (*Urtica dioica*), Rosemary Oil (*Rosmarinus officinalis*), Rue (*Ruta graveolens*).

Antigens

The adjuvant compositions disclosed herein may be administered in combination with one or more antigens. Any antigen against which it is desirable to induce an immune response may be used. Such an antigen may be obtainable from virus, fungi, or bacteria or other human and/or animal pathogens, or cancer cells. The antigen may be an allergen. Full length protein or a fragment thereof as well as modified or unmodified protein may be used as antigen. Antigens also include polysaccharides. In some cases, the antigen may be encoded by a DNA or RNA, e.g., derived from a pathogen or cancer cells.

Cancer Antigens.

Many human cancers express cell surface molecule that are specific to the cancer cell, i.e., they are not expressed at a detectable level or a significant level by normal human somatic cells. Examples of such antigens include but are not limited to the following: various glycolipids and polysaccharides, Alpha-fetoprotein (AFP) and Cancer Antigens CA125, CA15-3, and CA19-9.

AFP:

Elevation of serum AFP to abnormally high values occurs in several malignant diseases—including nonseminomatous testicular cancer and primary hepatocellular carcinoma—and some benign ones, including hepatitis and cirrhosis.

CA125:

Cancer Antigen 125 (CA125) is a surface antigen associated with epithelial ovarian cancer, and to date CA125 is the most sensitive marker for residual epithelial ovarian cancer. CA125 may also be elevated in patients with lung, cervical, fallopian tube, and uterine cancer and endometriosis.

CA15-3:

Cancer antigen 15-3 (CA15-3) is useful for monitoring breast cancer patients post-operatively for recurrence, particularly metastatic diseases. CA15-3 has been shown to be useful in early detection of relapse of ovarian cancer. CA15-3 levels are also increased in colon, lung, and hepatic tumors.

CA19-9:

Serum CA19-9 level is frequently elevated in subjects with certain gastrointestinal malignancies, such as pancreatic, colorectal, gastric and hepatic carcinomas. A persistently rising serum CA 19-9 value may be associated with progressive malignant disease and poor therapeutic response. A declining CA 19-9 value may be indicative of a favorable prognosis and good response to treatment.

Prion Antigens.

Transmissible spongiform encephalopathies (TSEs) are a group of neurodegenerative diseases characterized by a rapidly progressive deterioration (in cognitive function and/or coordination) which always leads to death. TSEs occur in humans and in animals. The most likely cause of the TSEs is the prion protein form designated PrPSc, named after scrapie, the oldest known form of prion disease, which originated in sheep and goats. How prions cause brain damage is unclear at present, but all hypotheses suggest that posttranslational modification of the native prion protein (PrPC) by PrPSc to form amyloid fibrils is a central event in pathogenesis.

In humans, Creutzfeldt-Jakob disease (CJD) is the most widespread TSE (incidence 1/million/year). Clinically, patients can be diagnosed as possible or probable CJD patients but neuropathological conformation is necessary to obtain a definite diagnosis. Neuropathological investigation is based on a triad of histological lesions: spongiosis, neuron loss, and reactive astrogliosis.

The prion protein (PrP) was initially described as an essential component of the infectious agents responsible for transmissible spongiform encephalopathies (TSE). TSE are a group of neurodegenerative disorders that include Creutzfeldt-Jakob disease and kuru in humans, bovine spongiform encephalopathy, sheep scrapie, and chronic wasting disease in deer and elk. Although the pathophysiology of TSE remains poorly understood, an almost invariable feature is the accumulation of an abnormal isoform of PrP (scrapie PrP, designated PrPSc) in infected tissues of affected individuals. PrP was found to be encoded by a unique gene of the host, Prnp (PRNP in humans), the structure of which is remarkably conserved between species. Its physiological product is expressed as a GPI-anchored membrane protein termed cellular PrP (PrPC), in many tissues at variable levels.

Pathogens.

The antigens for use in combination with the adjuvant compositions described herein include antigens derived from any pathogens including viruses, bacteria or fungi, or cancers. Such antigens include, for instance, the structural as well as nonstructural proteins of a pathogen, such as Env, Gag and Pol of HIV or F protein of RSV, or HA of influenza, in their native form or in a form optimized for enhanced immunogenicity.

Other antigens which may be included in the adjuvant compositions are: A protein antigen from *N. meningitidis* serogroup B, such as those in International patent application publications: WO99/24578; WO99/36544; WO99/57280; WO00/22430; and WO96/29412, for example; an outer membrane vesicle (OMV) preparation from *N. meningitidis* serogroup B, such as those disclosed in. International patent application WO0152885; an oligosaccharide antigen from *N. meningitidis* serogroup A, C, W135 and/or Y; A saccharide antigen from *Streptococcus pneumoniae*, an antigen from hepatitis A virus, such as inactivated virus, an antigen from hepatitis B virus, such as the surface and/or core antigens, an antigen from hepatitis C virus, *Bordetella pertussis*, such as pertussis holotoxin (PT) and filamentous haemagglutinin (FHA) from *B. pertussis*, optionally also in combination with pertactin and/or agglutinogens 2, a diphtheria antigen, such as a diphtheria toxoid, a tetanus antigen, such as a tetanus toxoid, a saccharide antigen from *Haemophilus influenzae* B, an antigen from *N. gonorrhoeae*) e.g. International patent application publication WO99/24578; WO99/36544; WO99/57280). Other antigens of interest include antigens from: *Chlamydia pneumoniae* (e.g. International patent application WO0202606; International patent application publications: WO99/27105; WO00/27994; WO00/37494), *Chlamydia trachomatis* (e.g. International patent application WO99/28475), *Porphyromonas gingivalis*, polio antigen(s) such as IPV or OPV, rabies antigen(s) such as lyophilised inactivated virus (e.g. 77, RabAvert™), measles, mumps and/or rubella antigens, influenza antigen(s), such as the haemagglutinin and/or neuraminidase surface proteins, the Respiratory syncytial virus, e.g. the F or the G proteins, the caliciviridae family of viruses, e.g. norovirus and sapovirus, the reoviridae family, e.g. Rotavirus, herpes simplex viruses, prions, the *Salmonella* bacteria, *Escherichia coli* bacteria, the *Vibrio cholera* bacteria, *Moraxella catarrhalis, Streptococcus agalactiae* (group B *streptococcus*) [e.g. International patent application PCT/GB01/04789], *Streptococcus pyogenes* (group A *streptococcus*) [e.g. International patent application PCT/GB01/04789], *Staphlylococcus aureus*, the Respiratory syncytial virus, e.g. the F or the G proteins, the caliciviridae family of viruses, e.g. norovirus and sapovirus, the reoviridae family, e.g. Rotavirus, herpes simplex viruses, *Salmonella* bacteria.

A saccharide or carbohydrate antigen may be conjugated to a carrier protein Exemplary carrier proteins are bacterial toxins or toxoids, such as diphtheria, cholera, *E. coli* heat labile or tetanus toxoids, CRM.sub.197 diphtheria toxoid, *N. men-*

*ingitidis* outer membrane protein [European patent application 0372501], synthetic peptides [European patent applications 0378881 & 0427347], heat shock proteins [International patent application WO93/17712], pertussis proteins [International patent application WO98/58668; see also EP 04711771, protein D from *H. influenzae* [International patent application WO00/563601], toxin A or B from *C. difficile* [International patent application WO00/61761], for example. Any suitable conjugation reaction can be used, with any suitable linker where necessary.

Nucleic Acid Encoding Antigen.

The immunomodulatory/adjuvant compositions disclosed may include a nucleic acid encoding antigen encoding a polypeptide antigen or a protein antigen as described above. Examples of antigens that can be encoded by nucleic acids and provided as DNA or RNA-based vaccines and vector vaccines include vaccines for HIV, herpes, hepatitis and influenza.

Examples of Compositions

Exemplary compositions are provided in Table 1 below.

response may be more suited to respond to extracellular bacteria and helminthic parasites and may also mediate allergic reactions, since IL-4 and IL-5 are known to induce IgE production and eosinophil activation.

Vitamin A (e.g., All-trans retinoic acid (ATRA), an acid derivation of Vitamin A) may be included in the adjuvant compositions if a higher Th-2 response is desired. In certain cases, it may be desirable to elicit a Th-1 type immune response. In these cases, the adjuvant compositions may include Vitamin C (e.g., ascorbate) and/or Vitamin D and/or Vitamin E and/or a flavonoid.

The adjuvant composition may include: a flavonoid and Vitamin A; or a flavonoid, Vitamin C and Vitamin A; or a flavonoid, Vitamin D and Vitamin A; or a flavonoid, Vitamin E and Vitamin A; or a flavonoid, Vitamin C and E and Vitamin A; or a flavonoid, Vitamin C and D and Vitamin A; or a flavonoid, Vitamin D and E and Vitamin A in the adjuvant compositions. It is understood that each of the foregoing adjuvant compositions include a pharmaceutically acceptable vegetable oil (e.g., mustard oil, corn oil, soybean oil, sun-

TABLE 1

| Adjuvant Composition | Pharmaceutically Acceptable Oil Carrier | Flavonoid (or derivative or salt thereof) | Vitamin (or derivative or salt thereof) |
|---|---|---|---|
| 1 | Mustard Oil (+/− AIT) | Catechin hydrate | Vitamin A |
| 2 | Mustard Oil (+/− AIT) | Catechin hydrate | Vitamin E |
| 3 | Mustard Oil (+/− AIT) | Catechin hydrate | Vitamin C |
| 4 | Mustard Oil (+/− AIT) | Catechin hydrate | Vitamin D |
| 5 | Mustard Oil (+/− AIT) | Catechin hydrate | Vitamin A + Vitamin E |
| 6 | Mustard Oil (+/− AIT) | Catechin hydrate | Vitamin A + Vitamin D |
| 7 | Mustard Oil (+/− AIT) | Catechin hydrate | — |
| 8 | Mustard Oil (+/− AIT) | — | Vitamin A |
| 9 | Mustard Oil (+/− AIT) | — | Vitamin E |
| 10 | Mustard Oil (+/− AIT) | — | Vitamin C |
| 11 | Mustard Oil (+/− AIT) | — | Vitamin D |
| 12 | Mustard Oil (+/− AIT) | — | Vitamin A + Vitamin E |
| 13 | Mustard Oil (+/− AIT) | — | Vitamin A + Vitamin D |
| 14 | Olive Oil (+/− AIT) | Catechin hydrate | Vitamin A |
| 15 | Olive Oil (+/− AIT) | Catechin hydrate | Vitamin E |
| 16 | Olive Oil (+/− AIT) | Catechin hydrate | Vitamin C |
| 17 | Olive Oil (+/− AIT) | Catechin hydrate | Vitamin D |
| 18 | Olive Oil (+/− AIT) | Catechin hydrate | Vitamin A + Vitamin E |
| 19 | Olive Oil (+/− AIT) | Catechin hydrate | — |
| 20 | Olive Oil (+/− AIT) | Catechin hydrate | Vitamin A + Vitamin D |
| 21 | Olive Oil (+/− AIT) | — | Vitamin A |
| 22 | Olive Oil (+/− AIT) | — | Vitamin E |
| 23 | Olive Oil (+/− AIT) | — | Vitamin C |
| 24 | Olive Oil (+/− AIT) | — | Vitamin D |
| 25 | Olive Oil (+/− AIT) | — | Vitamin A + Vitamin E |
| 26 | Olive Oil (+/− AIT) | — | Vitamin A + Vitamin E |

The adjuvant compositions 1-26 described above are exemplary and may include additional components, such as, an additional oil carrier, e.g., sunflower seed oil, coconut oil, soybean oil. In other embodiments, compositions 1-26 described above do not contain additional oil carriers, e.g., sunflower oil, coconut oil, soybean oil.

The adjuvant compositions 1-26 described in Table 1 as well as other adjuvant compositions described in the specification may include additional components, such as, additives, e.g., antigens, preservatives, colorants, flavorants, buffers, salts, etc.

Components of the Adjuvant Compositions and their Relative Amounts

The adjuvant compositions described herein may be used to induce an immune response, such as, a Th-1 response. Th-1 response may be particularly suited to respond to viral infections, intracellular pathogens, and tumor cells because it includes IL-2 and IFN-γ, which activate CTLs.

The adjuvant compositions described herein may be used to induce an immune response, such as, a Th-2 response. Th-2 flower oil, etc). In addition, it is understood that each of the foregoing compositions may include the vitamin named or a salt or derivative thereof. Similarly, the flavonoid may be a flavonoid or a salt or derivative thereof.

In certain embodiments, the inclusion of a pharmaceutically acceptable vegetable oil (e.g., mustard oil), a flavonoid, and a vitamin (such as, Vitamin A, C, D and/or E) in the adjuvant compositions may produce an enhanced immune response (for example, synergistic effect) compared to the effect of an adjuvant composition that includes a pharmaceutically acceptable vegetable oil (e.g., mustard oil) and a flavonoid or a pharmaceutically acceptable vegetable oil (e.g., mustard oil) and a vitamin (such as, Vitamin A, C, D and/or E).

The adjuvant compositions disclosed herein may include mustard oil or another pharmaceutically acceptable oil carrier. Pharmaceutically acceptable oil carrier with rubefacient properties, for example mustard oil, is suitable for preparation of adjuvant compositions for administration through epithelial cells of the mucosal membranes or the skin or directly injected by e.g. intra-muscular or intra-dermal administrations.

The volume of pharmaceutically acceptable oil carrier, e.g., mustard oil, used in liquid form in the adjuvant compositions described herein may be in the range of 1-95% of the total volume of an adjuvant composition. Thus, in certain cases, the pharmaceutically acceptable oil carrier may make up 1%, 5%, 10%, 20%, 30%, 40%, 50%, 60%, 70%, 80%, 90%, or 95% by volume of the total volume of a subject adjuvant composition.

The amount of a vitamin (or its salt or derivative) that may be included in the subject adjuvant compositions may be determined based on the body weight of the subject. In general, the recommended daily allowance may be used to ascertain the amount of vitamin that may be present in the subject adjuvant compositions.

For example, the amount of vitamin A that may be included in the subject adjuvant compositions may be in the range of 1-250 µg/kg body weight, e.g., 1 µg/kg, 5 µg/kg, 10 µg/kg, 20 µg/kg, 30 µg/kg, 50 µg/kg, 70 µg/kg, 90 µg/kg, 110 µg/kg, 130 µg/kg, 150 µg/kg, 170 µg/kg, 190 µg/kg, 210 µg/kg, 230 µg/kg, or 250 µg/kg body weight.

For example, the amount of vitamin C that may be included in the subject adjuvant compositions may be in the range of 1-100 mg/kg body weight, e.g., 1, 5, 10, 15, 30, 50, 70, 80, 90, or 100 mg/kg body weight.

For example, the amount of vitamin D that may be included in the subject adjuvant compositions may be in the range of 0.01-10 µg/kg body weight, e.g., 0.01, 0.5, 1, 2, 5, 7, 8, 9, or 10 µg/kg body weight.

For example, the amount of vitamin E that may be included in the subject adjuvant compositions may be in the range of 0.01-10 µg/kg body weight, e.g., 0.01, 0.05, 0.1, 0.5, 1, 2, 5, 7, 8, 9, or 10 µg/kg body weight.

The amount of a flavonoid (or its salt or derivative) that may be included in the subject adjuvant compositions may be determined based on the body weight of the subject. The amount of the flavonoid, e.g., catechin (such as catechin hydrate), may be in the range of 1-100 mg/kg body weight of a subject, e.g., 1, 5, 10, 15, 30, 50, 70, 80, 90, or 100 mg/kg body weight.

The adjuvant compositions may be in the form of a suspension, tablet (to be swallowed or chewed), fast-dissolving tablets or gels or strips, capsule, powder, gel, cream, lotion, ointment, aerosol or the like.

An exemplary adjuvant composition for administration to a human subject may include 3-80% vol/vol of mustard oil, e.g., 3%, 10%, 15%, 20%, 25%, 30%, 40%, 50%, 60%, 70%, or 80% vol/vol of mustard oil.

An exemplary adjuvant composition for administration to a human subject may include 0.1-100 mg of Vitamin A, e.g., 0.1, 0.5, 1, 5, 10, 15, 30, 50, 70, 80, 90, or 100 mg of Vitamin A.

An exemplary adjuvant composition for administration to a human subject may include 0.1-400 mg of Vitamin E, e.g., 0.1, 0.5, 1, 5, 10, 15, 30, 50, 70, 80, 90, 100, 200, 300, or 400 mg of Vitamin E.

An exemplary adjuvant composition for administration to a human subject may include 0.1-2000 mg of Vitamin C, e.g., 0.1, 0.5, 1, 10, 30, 100, 130, 200, 300, 600, 900, 1000, 1300, 1500, 1800, or 2000 mg of Vitamin C.

An exemplary adjuvant composition for administration to a human subject may include 0.1-2000 mg of Catechin hydrate, e.g., 0.1, 0.5, 1, 10, 30, 100, 130, 200, 300, 600, 900, 1000, 1300, 1500, 1800, or 2000 mg of Catechin hydrate.

An exemplary adjuvant composition for administration to a human subject may include 0.001-10 mg of AIT, e.g., 0.001, 0.005, 0.01, 0.05, 0.1, 0.5, 1, 2, 5, 7, 8, 9, or 10 mg of AIT.

As used in herein vol/vol refers to the volume of a component in the total volume of the adjuvant composition.

Th1-type immune response can be induced in mammals by administration of certain immunomodulatory polynucleotides. The immunomodulatory polynucleotides include sequences referred to as immunostimulatory sequences ("ISS"), often including a CG dinucleotide. See, e.g., PCT Publications WO 98/55495, WO 97/28259, U.S. Pat. Nos. 6,194,388 and 6,207,646. Thus, in certain embodiments, the subject adjuvant compositions may include ISS.

In certain embodiments, the subject adjuvant compositions may include an emulsifier (such as, lecithin, or a surfactant, e.g., detergents) as described above. The concentration of an emulsifier in the adjuvant composition is dependent on different factors. For example, the higher the concentration of the pharmaceutically acceptable oil in the adjuvant composition the more emulsifier is required. In general, the concentration of a surfactant or other emulsifier in the subject adjuvant composition is from 1.5% to 5% v/v, or 1.5% to 3% v/v, or 1.5% to 2.5%, or 2% v/v. When more than one surfactant is used, the sum of the concentrations of all surfactants used in the adjuvant composition is also from 1.5% to 5%, or 1.5% to 3%, or 1.5% to 2.5%, or 2% v/v.

The adjuvant compositions disclosed herein may not include an antigen. An adjuvant composition that does not include an antigen may be used to generally and non-specifically enhance immune responses, for example to serve as a general immunopotentiator to be taken daily. Alternatively, an adjuvant composition that does not include an antigen can be administered in conjunction with an antigen, i.e., before, simultaneously, or after vaccinations.

Adjuvant Compositions Including Antigen

In certain embodiments, the subject adjuvant compositions may include one or more antigens.

The concentration of antigen in adjuvant compositions can vary widely, and will be selected primarily based on fluid volumes, viscosities, body weight and the like in accordance with the particular mode of administration selected and the subject's needs. The concentration of an antigen in the pharmaceutical formulations can vary widely, i.e., from less than about 0.1%, usually at or at least about 2% to as much as 20% to 30% or more by weight/volume, and will be selected primarily by nature of the antigen, fluid volumes, viscosities, etc., in accordance with the particular mode of administration selected. In certain embodiments, the antigen may be 0.1%-30% w/v of the adjuvant composition, for example, 0.1%-25%, 0.5%-20%, 1%-15%, 2%-10%, 3%-8%, or 5%-6% w/v of the adjuvant composition.

Method of Making Adjuvant Composition

The components of the subject adjuvant composition may be obtained from a variety of sources using a number of methods. Alternatively, the components may be synthesized chemically. In certain cases, the components may be made isolated from a natural source and may be additionally modified, e.g., chemically modified. For example, mustard oil may be extracted from mustard plant seeds. Alternatively, the pharmaceutically acceptable vegetable oil carrier may be purchased from a vendor. Vitamins A, C, D, and E may be purchased from Sigma Aldrich chemical company, prepared and produced by standard biochemical methods. The flavonoids, e.g., catechins, for example, catechin hydrate, may be purchased from Sigma Aldrich chemical company, prepared and produced by standard biochemical methods.

In general, Catechins may either be extracted from green tea or synthesized chemically. Korean and Chinese green tea, and pu-erh, Indian black, Longjing, Tieguanyin, Bamboo, Jasmine, Oolong, Flower, Red teas may be used for extracting catechins, such as, epigallocatechin, catechin, epicatechin, epigallocatechin gallate and epicatechin gallate. Chinese green tea is a rich source of catechin. Green tea is a better source of catechin compared to the other types of tea.

Vitamin A (e.g., retinoic acid), Vitamin D (e.g., Calcitriol (1,25-Dihydroxycholecalciferol), Vitamin E (e.g., alpha-tocopherol) and catechin hydrate may be dissolved in ethanol, for example, 200 proof ethanol. Vitamin C may be dissolved in an alkaline solution such as sodium bicarbonate buffer. An antigen may be dissolved in water, a buffer (e.g., PBS), or saline solution. A stock solution of the individual components of the adjuvant composition may be made and the appropriate volumes of the components may then be mixed together to obtain the subject adjuvant composition. The total volume of the subject adjuvant composition may be adjusted with PBS or saline.

In certain embodiments, a pharmaceutically acceptable oil and a falvonoid and optionally a vitamin may be mixed together in amounts as described above along with a surfactant such as Tween®-80. Before administrating, the adjuvant composition may be emulsified by repeatedly withdrawing and releasing the mixture of a pharmaceutically acceptable oil, a surfactant(s), and another component(s).

The components of the adjuvant compositions may be sterilized prior to admixing or after forming the adjuvant compositions. The adjuvant compositions may be mixed with a gel, or formulated into microparticles, etc. before administration.

The adjuvant compositions disclosed herein may be formulated into a spray (e.g., nasal spray), drops (e.g., nasal drops), gel, powder, tablets or capsules, patch, and the like. Of particular interest are adjuvant compositions suitable for administration via inhalation including but not limited to, liquid suspensions for forming aerosols as well as powder forms for dry powder inhalation delivery systems. Devices suitable for administration by inhalation of subject adjuvant composition include, but are not limited to, atomizers, vaporizers, nebulizers, and dry powder inhalation delivery devices.

The adjuvant compositions disclosed herein may be formulated into liquids or emulsions for injecting using a parenteral route, e.g., intravenous, intramuscular, subcutaneous.

Method of Using Adjuvant Compositions

The present disclosure provides methods for modulating an immune response in a subject, such as, stimulating a cellular and/or a humarl immune response. The adjuvant compositions disclosed herein can be useful for prophylaxis and/or treatment of various infections and neoplastic diseases.

Conditions

In certain embodiments, the adjuvant compositions disclosed herein may be find use in the context of administering an antigen, as a vaccine. The vaccine may be a prophylactic vaccine or a therapeutic vaccine. A prophylactic vaccine is given before infection to prevent disease, whereas a therapeutic vaccine is give after the onset of infection or disease. A prophylactic vaccine comprises one or more epitopes associated with a disorder for which the subject may be at risk (e.g., *M. tuberculosis* antigens as a vaccine for prevention of tuberculosis). Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients.

The adjuvant composition may be given in conjunction with the antigen (e.g., in the same composition or a simultaneously using separate compositions) or the adjuvant composition may be administered separately (e.g., at least 12 hours before or after administration of the antigen). In certain embodiments, the antigen(s) is admixed with the adjuvant composition.

Administration of the subject adjuvant composition and antigen may result in amelioration of one or more symptoms or a later onset of one or more symptoms of the disorder which the vaccine is intended to treat. As will be apparent to one of skill in the art, the exact symptoms and manner of their improvement will depend on the disorder sought to be treated. For example, where the therapeutic vaccine is for tuberculosis, administration of adjuvant composition with antigen may result in reduced or delayed onset of coughing, pleural or chest wall pain, fever, and/or other symptoms known in the art. Where the vaccine is an allergen used in allergy desensitization therapy, the administration of adjuvant composition with antigen may result in a reduction or a delay in onset of the symptoms of allergy (e.g., reduction in rhinitis, allergic conjunctivitis, circulating levels of IgE, and/or circulating levels of histamine).

The subject adjuvant composition may also be used prophylactically to increase resistance to infection by a wide range of bacterial or viral pathogens, including natural or genetically modified organisms employed as agents of biological warfare or bio-terrorism.

Other embodiments relate to immunomodulatory therapy of subjects having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type immune response results in the death of tumor cells, either by direct action of cellular immune system cells (e.g., CTLs) or components of the humoral immune system, or by bystander effects on cells proximal to cells targeted by the immune system including macrophages and natural killer (NK) cells.

The adjuvant composition disclosed herein can also be administered to subjects with infectious diseases caused by extracellular pathogens (e.g., bacteria or protozoans) or by intracellular pathogens (e.g., viruses).

In certain embodiment, a subject suffering from a disorder associated with a Th2-type immune response, such as (without limitation) allergies, allergy-induced asthma, atopic dermatitis, eosinophilic gastrointestinal inflammation, eosinophilic esophagitis, and allergic bronchopulmonary aspergillosis may be treated by administering an adjuvant composition disclosed herein. For example, an adjuvant composition comprising a pharmaceutically acceptable oil carrier, a flavonoid and at least one vitamin C, D and E may be administered to the subject suffering from a disorder associated with a Th2-type immune response increasing levels of one or more Th1-type response associated cytokines, which may result in a reduction of the Th2-type response features associated with the subject's response to the allergen. Immunomodulation of a subject with Th2-type response associated disorders results in a reduction or improvement or delay in the onset of one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for "rescue" inhaler therapy (e.g., inhaled albuterol administered by metered dose inhaler or nebulizer).

Route of Administration

The adjuvant compositions disclosed herein may be administered to a subject via a number of routes of administration. Exemplary routes of administration include mucosal, e.g., oral, sublingual, intra-nasal, inhalation, ocular, intra-vaginal, intra-rectal; and systemic, e.g., intra-muscular, intra-dermal, trans-dermal, intraperitoneal, subcutaneous or transcutaneous. In certain embodiments, a combination of at least two routes of administration may be used to induce an immune response. For example, a combination of a mucosal route and a systemic route of administration may be used.

In certain embodiments, the adjuvant compositions described herein are not administered systemically.

The route of administration may vary based on the individual subject and the stage of the disease and other factors evident to one skilled in the art.

In certain embodiments, the adjuvant compositions described herein may be administered through the mucosal surface without breaking the mucosal surface.

The subject adjuvant compositions may be used with or without an antigen(s). When used with an antigen, the adjuvant composition and the antigen may be administered simultaneously or the adjuvant composition may be administered before or after the administration of the antigen. When used with an antigen, the antigen may be mixed with the adjuvant composition.

The adjuvant compositions disclosed herein may be provided as micro- or nano-particles in gel or tablet (such as, fast dissolving) forms. Such formulations may be administered via oral or sublingual routes, for example. For intra-nasal administration, the adjuvant compositions may be formulated as nasal sprays in an emulsion form or drops, for example. For transcutaneous administration, adjuvant compositions may be given in a gel, lotion or ointment form. For systemic injections, the adjuvant compositions can be given formulated as an emulsion and/or micro/nanoparticles. For rectal administration, the adjuvant compositions can be formulated as suppository or gels, for example. For vaginal administration, the adjuvant compositions formulated as gel, emulsion, ointment, for example.

In certain embodiments, the adjuvant compositions disclosed herein may be administered to a subject via a combination of different routes in the order indicated below:
i. systemic, mucosal;
ii. systemic, systemic, mucosal, mucosal;
iii. systemic, mucosal, systemic;
iv. mucosal, mucosal, systemic, systemic;
v. mucosal, systemic, systemic;
vi. mucosal, systemic, mucosal, for example.

When an adjuvant composition is administered systemically or mucosally more than once, the two or more systemic or mucosal administrations may be by the same systemic (for example, two intramuscular injections) or mucosal route (two IN/SL administrations) or different (for example, one intramuscular injection and one intravenous injection; one IN administration and one SL administration).

Dosages

The dosage of the adjuvant compositions described herein to be administered to a subject comprising may be determined based on the route of administration and body weight and may range from 0.001 ml/kg body weight to 1 ml/kg body weight. The number of times an adjuvant composition is administered may vary and may be determined based upon numerous factors. These factors are evident to a person of skill in the art and may include, the disease to be prevented or treated, the type of pathogen or cancer, the structural nature of the antigen, the route of administration, the level of immune response induced in the subject, the type of immune response, etc.

Subjects

The adjuvant compositions described herein may be used to elicit an immune response in a variety of subjects capable of mounting an immune response. In certain cases, the adjuvant compositions described herein may be administered to any member of the subphylum chordata, including, mammals (humans, other non-human primates, domesticated animals, e.g., livestock), avians, fishes, or any other animal in need thereof. In certain cases, the adjuvant compositions may be administered to humans. In certain cases, the adjuvant compositions may be administered to cows. In certain cases, the adjuvant compositions may be administered to chickens, horse, sheep, goats. In certain cases, the adjuvant compositions may be administered to porcines. In certain cases, the adjuvant compositions may be administered to cats and dogs.

Detection of Immune Response

Modulation of an immune response may be humoral and/or cellular, and may be measured using standard techniques in the art. An immune response in a subject can be detected in any number of ways, including measuring expression levels of antigen-specific antibodies, one or more of IFN-gamma, IFN-alpha, IL-2, IL-12, TNF-alpha, IL-6, IL-4, IL-5, IL-10, IL-12, IL-13, IL-15, IL-18, IL-22, and other cytokines as well as detecting responses such as B cell proliferation, activation of specific populations of lymphocytes such as CD4$^+$T cells, NK cells or CTLs, and dendritic cell and macrophage maturation and activation.

Methods for measuring specific antibody responses include enzyme-linked immunosorbent assay (ELISA) and are well known in the art. Measurement of numbers of specific types of lymphocytes such as CD4$^+$T cells can be achieved, for example, with fluorescence-activated cell sorting (FACS). Cytotoxicity and CTL assays can be as described in Raz et al. (1994) Proc. Natl. Acad. Sci. USA 91:9519-9523, for example. Cytokine concentrations can be measured, for example, by ELISA. These and other assays to evaluate the immune response to an immunogen are well known in the art. See, for example, SELECTED METHODS IN CELLULAR IMMUNOLOGY (1980) Mishell and Shiigi, eds., W.H. Freeman and Co.

Kits

Kits that include one or more sterile containers of components of the adjuvant compositions described herein are also provided. Individual components may be present in separate sterile containers or two or more components may be present in a single container. Optionally, the kit may also include a container containing a desired antigen(s).

In some embodiments, the sterile containers may optionally have an access port(s) for withdrawing a specific volume/amount of a component, for example, a port for introducing a syringe to withdraw a certain volume of a pharmaceutically acceptable oil.

In some embodiments, the containers of the components of the adjuvant compositions described herein may not be sterile but are reasonably clean.

The kits may further include a suitable set of instructions, generally written instructions, relating to the use of the adjuvant composition for immunomodulation (e.g., ameliorating symptoms of an infectious disease, increasing IFN-gamma levels, increasing IFN-alpha levels, or ameliorating an IgE-related disorder).

The kits may comprise the components of the adjuvant composition packaged in any convenient, appropriate packaging. For example, if a component is a dry formulation (e.g., freeze dried or a dry powder), a vial with a resilient stopper may be used, so that the component may be easily resuspended by injecting fluid through the resilient stopper. Ampoules with non-resilient, removable closures (e.g., sealed glass) or resilient stoppers may be used for liquid component(s) of the adjuvant composition. Also contemplated are packages for use in combination with a specific device, mucosal administration devices, such as, an inhaler, nasal administration device (e.g., an atomizer) or eye drops.

The instructions relating to the use of adjuvant composition generally include information as to dosage, dosing schedule, and route of administration for immunomodulation. The containers of containing the components of adjuvant composition or the premixed adjuvant composition may be unit doses, bulk packages (e.g., multi-dose packages) or sub-unit doses. Instructions supplied in the kits disclosed herein are typically written instructions on a label or package insert (e.g., a paper sheet included in the kit), but machine-readable instructions (e.g., instructions carried on a magnetic or optical storage disk) may also be included.

EXAMPLES

The following example is provided to further illustrate the advantages and features of the present invention, but is not intended to limit the scope of the invention. While they are typical of those that might be used, other procedures, methodologies, or techniques known to those skilled in the art may alternatively be used.

Materials and Methods

The following materials and methods were used in Examples 1-4.

Adjuvants and vaccine preparations.

Recombinant HA protein of A/Calcdonia/20/99 (H1N1)-like virus (stock concentration 0.33 µg/µl) was used at 0.5 µg per dose. Vitamin A (VA; Retinoic acid, Sigma-Aldrich; Cat# R2625), Vitamin E (VE; alpha tocopherol, Sigma-Aldrich/Fluka Biochemika; Cat#95240) and Catechin Hydrate (Cat; Sigma-Aldrich, C1251, synonym: (+)-Cyanidol-3, (2R,3S)-2-(3,4-Dihydroxyphenyl)-3,4-dihydro-1(2H)-benzopyran-3,5,7-triol) were dissolved in 200 proof absolute ethanol (Sigma-Aldrich, Cat#459844). The stock concentration was 3 µg/µl for VA, 2000 µg/µl for VE, and 50 µg/µl for Cat Hydrate. Vitamin C (VC; Sigma-Aldrich, Cat# A4544) was dissolved in Sodium Bicarbonate buffer (pH 10.6) at the concentration of 100 µg/µl (pH 5.5). Mustard seed oil (MO) was purchased from Botanic Oil Innovations Inc. (Spooner, Wis.).

The amount used for each dose of vaccination was 30 µg for VA, 500 µg for VC, 2000 µg for VE, and 120 µg for Cat. The total volume for each IM thigh dose was 100 µl which was adjusted with Dulbecco's phosphate buffered saline (PBS) (Cat#21-030-CV). All vaccines were prepared with endotoxin free reagents and in endotoxin free 2.0 ml tubes (Eppendorf biopur safe-lock microcentrifuge tubes).

A total of 22 different adjuvant combinations with vaccine were prepared. The first 11 groups were prepared without MO, and the last 11 groups were prepared with MO (50% of the total volume). For all combinations with MO, Tween®-20 (Sigma, Cat# P1379) was added at a final concentration of 0.1% for emulsification. The combinations with MO were emulsified by repeatedly withdrawing-releasing for at least 15 times using BD's ½ CC ½ In. 27G tuberculin syringes (Cat#305620). Four doses were prepared for each combination.

The 22 groups of combinations of HA vaccines were as shown in Table 2 below. Each group includes recombinant HA protein.

TABLE 2

| GROUP | VACCINE COMPOSITION |
|---|---|
| 1 | VA |
| 2 | VC |
| 3 | VE |
| 4 | Cat |
| 5 | VA + VC |
| 6 | VC + VE |
| 7 | VC + Cat |
| 8 | VE + Cat |
| 9 | VC + VE + Cat |
| 10 | VA + VC + VE + Cat |
| 11 | PBS |
| 12 | VA + MO |
| 13 | VC + MO |
| 14 | VE + MO |
| 15 | Cat + MO |
| 16 | VA + VC + MO |
| 17 | VC + VE + MO |
| 18 | VC + Cat + MO |
| 19 | VE + Cat + MO |
| 20 | VC + VE + Cat + MO |
| 21 | VA + VC + VE + Cat + MO |
| 22 | MO |

Animals and Immunizations.

Sixty-six female BALB/c mice of 6-8 weeks of age were randomly divided into 22 groups (3 mice/group). The mice were maintained according to IACUC guidelines in the vivarium of Murigenics Inc. (Vallejo, Calif. 94592). The mice were anesthetized with isoflurane, and vaccinated by intramuscular (IM) injections at both thighs using the same tuberculin syringes used for emulsification. Each mouse received 100 µl of the vaccine preparations, i.e., 50 µl at each thigh.

Test of Cytokines in Sera Collected One Day after Immunization.

At one day post vaccination, mice were bled retro-orbitally and serum was prepared from individual mice. The sera were tested for TNFα and IL-12 using ELISA Max™ Deluxe sets from Biolegend (Cat#433606 and Cat#430906, respectively) following the manufacturer's instructions. To enhance the sensitivity of the tests, an ELAST® ELISA Amplification System by PerkinElmer (Cat#NEP116E001EA) was used. Briefly, after the avidin-HRP step in the Biolegend kits, biotinylated tyramide (10 µl/ml in tyramide diluent) was added. The plates were incubated for 15 minutes at room temperature. After washing with PBS-Tween20 (PBS-T) 5 times, streptavidin-HRP was added at 2 µl/ml in blocking solution (1% goat serum and 0.02% Tween-20 in PBS). After incubation for 30 minutes at room temperature, the plates were washed 5 times with PBS-T and the substrate TMB (BioFX Laboratories, Cat# TMBS-0100-01) was added. The color development was watched closely and stopped immediately with 1N $H_2SO_4$ when background color started to appear in blank wells. Absorbance was read at 450 nm using a Molecular Devices UV max kinetic microplate reader (Sunnyvale, Calif.). The concentration of each cytokine in each sample was determined using the Softmax Pro software (Molecular Devices, Sunnyvale, Calif.) and based on standards provided by the kit manufacturer.

Test of Serum Antibodies by ELISA.

At 3 weeks post vaccination, the mice were bled retro-orbitally. Sera were collected for individual mouse and were kept at −20° C. before tests. For IgG1 ELISA, nunc Maxisorp® 96-well microplates were coated with 100 µl of the recombinant HA protein at the concentration of 0.66 µg/ml in PBS at 4° C. overnight. After washing 4 times with PBS-T, the plates were blocked with 200 µl blocking solution (1% goat serum, 0.02% Tween-20 in PBS) for 1 hour at room temperature. The serum samples were diluted 1/600 in the blocking solution initially and 3-fold serial dilutions were made in each column of 96-well microplates for each sample. Column 1 was used as blank. A positive reference serum and a negative reference serum were diluted in the same way in column 2 and 3, respectively. After addition and dilution of the serum samples, the plates were incubated for 2 hours at room temperature. The plates were then washed 5 times with PBS-T followed by addition of 100 µl goat anti-mouse IgG1-HRP conjugate (Southern Biotech, Cat#1070-05) diluted 1/8000 in blocking solution. The plates were incubated for 1 hour at room temperature. After washing 5 times with PBS-T, 100 µl TMB substrate was added for color development. The color development was stopped at 30 minutes by addition of 100 µl of 1N sulfuric acid. The plates were read at 450 nm using a microplate reader (Molecular Devices, Sunnyvale, Calif.). The cutoff value was determined as two and half times of the background value (average value of blank wells). The titer of each serum sample was calculated automatically using the software based on log-logit curves. For IgG2a titration, all the procedures and reagents were the same as for IgG1 ELISA except for the secondary antibody conjugate. A goat anti-mouse IgG2a-HRP conjugate (Southern Biotech, Cat#1080-05) diluted at 1/8000 was used. For IgA titration, the procedures and reagents used were the same as above except that the serum samples were diluted initially at 1/20 followed by 3-fold serial dilutions in each column and a goat anti-mouse IgA-Biotin (Southern Biotech, Cat#0106-08) diluted 1/8000 was used. An additional step with avidin-HRP was also needed.

Splenocyte Cultures and Tests of Cytokines in Supernatants by ELISA.

One week post $2^{nd}$ vaccination the 66 mice were sacrificed, and spleens (SP) and vaginal lavages were collected. Each individual spleen was pressed through Falcon 70 um nylon mesh (Cat#353910) followed by rinsing of the mesh with about 4.5 ml complete RPMI 1640 media with 5% FBS and antibiotics (complete RPMI). The cells were collected into a 50 ml centrifuge tube and were transferred into a 5 ml Nalgene tube (Cat#5000-0050). After spinning for 5 minutes at 4° C. at 600×g in a Eppendorf Benchtop centrifuge (5702R), the cells were gently resuspended in 4.5 ml complete RPMI. The cells were centrifuged and resuspended again. For cell counting, 20 µl cell suspensions were mixed with 180 µl PBS to make a 1/10 dilution, and 10 µl of the diluted cell suspension was mixed with 10 µl trypan blue, and 10 µl of the mixture was used for counting the cells with a hemocytometer. After counting, the cell concentration in each spleen sample was diluted to a final concentration of $2 \times 10^6$/ml.

For cell culture, Corning 24-well cell culture plates (Cat#3526) were used. 0.5 ml of the cells was added to each well ($1 \times 10^6$ cells/ml). Two wells were used for each sample. One well contained 0.5 ml complete RPMI 1640 and the other well contained 0.5 ml complete RPMI 16490 with 2 µg/ml HA protein resulting in the final concentration of 1 µg/ml. After incubation at 37° C. in a $CO_2$ incubator for 24 hours, cells and supernatants (SN) were harvested and were centrifuged for 5 minutes at 600×g. The supernatants were collected in 2 ml microcentrifuge tubes and stored at –20° C. and assayed within a week.

To test cytokines in the supernatants, IFNγ, IL-5, IL-10 were tested using ELISA Max™ Deluxe sets from Biolegend (Cat#430806, Cat#431206, and Cat#431406, respectively) following the manufacturer's instructions. To enhance the sensitivity of the tests, the ELAST® ELISA Amplification System by PerkinElmer was used and the procedure was the same described above.

Test of IgG1 and IgA in Vaginal Lavages by ELISA.

Vaginal washes about 100 µl were collected from individual mouse using a pipetman by aspirating about 100 µl PBS inside the vaginal vault 5-7 times. The vaginal lavages were kept on dry ice for later use. Spleens were removed aseptically from individual mice following the collection of vaginal lavages and were immediately placed into 4.5 ml cold RPMI 1640 basic medium (UCSF Cell culture facility). Vaginal washes collected above were thawed and vortexed followed by centrifugation at 3000×g for 5 minutes. The 3 vaginal lavages within each group were pooled and tests were run for individual group. The ELISA tests were performed in a similar way to that described for serum IgG1 and IgA above except that the initial dilution for both IgG1 and IgA was 1/3 followed by 3-fold serial dilutions. The tests also employed the PerkinElmer ELAST® ELISA Amplification System described above to increase sensitivity. For IgG1, the biotinylated tyramide was added after the Goat anti mouse IgG1-HRP step. For IgA, the biotinylated tyramide was added after the avidin-HRP step.

Example 1

Immune-Modulation Following a Single Intramuscular (IM) Injection

A significant enhancement of serum IgG1 antibody responses following vaccinations with HA plus selected components was observed. While HA plus MO enhanced the responses compared to HA alone, there was a further enhancement with other components. In general, addition of MO enhanced the IgG1 responses compared to single vitamins, cat or cat+VE (FIG. 1). The enhancement by MO compared to vaccinations with HA in PBS alone, was the highest in the group vaccinated with HA+cat+MO, which induced a 15 fold enhancement, followed by HA+cat+VE+MO and HA+VA+MO (FIG. 1). The groups of mice vaccinated with the other compositions listed in Table 1 did not show enhanced serum IgG1 antibody responses compared to HA in PBS alone. These results demonstrate that of all the 22 compositions tested, cat plus MO mixed with HA induced the highest IgG1 responses. Interestingly, the adjuvant compositions with vitamin C appeared to suppress immune response. However, it is hypothesized that the suppression of immune response may be an artifact caused by the high dose of vitamin C administered to the mice or the one pH unit difference between adjuvant compositions with vitamin C compared to those without vitamin C.

Serum anti-HA IgG2a responses were measured as a potential surrogate for TH1 response. In contrast to the IgG1 responses, the highest serum IgG2a responses were measured in the group vaccinated with VA alone (FIG. 1).

Example 2

Immune-Modulation Following Two Intramuscular (IM) Injections

Compared to the data obtained at 3 weeks after a single IM vaccination, at one week after the second IM vaccination, serum anti-HA IgG1 responses generally increased at least 10 fold (FIG. 2). Similar to the results after a single IM vaccination, anti-HA IgG1 responses were higher in the groups that were vaccinated with HA+MO, HA+MO+VA, and HA+MO+Cat, compared to vaccinations with HA in PBS alone. In addition, the group that was vaccinated with HA+MO+VE also showed enhanced IgG1 responses compared to HA in PBS alone. Addition of MO to any of the groups enhanced the IgG1 responses. None of the other compositions listed in Table 1 resulted in the enhancement of the IgG1 responses compared to HA in PBS alone (data not shown). These data show that following two IM vaccinations, compared to vaccinations with HA in PBS alone, serum anti-HA responses were significantly enhanced when MO was mixed with cat, VA or VE.

After the second IM vaccination with HA+VA+MO the IgG2a responses were enhanced compared to the IgG2a responses measured after the first vaccination (FIGS. 1 and 2).

To determine whether vaccinations with the various components resulted in heavy chain isotype switch to IgA, serum anti-HA IgA responses were determined. Groups of mice vaccinated with HA+VA+MO, HA+VC+MO, HA+Cat+MO, and HA+VE+cat showed an enhancement of serum IgA response compared to HA in PBS alone (FIG. 3).

None of other compositions listed in Table 1 resulted in enhanced serum IgA responses.

These data indicate the utility of VA+MO and Cat+MO as adjuvants that induce antigen-specific isotype switch to IgA and IgG, respectively.

Example 3

Mucosal Immune Response Following Intramuscular (IM) Injections

Responses Measured in Vaginal Lavages.

The female genital tract is a major mucosal tissue and serves as the route of transmission of many important bacterial and viral agents. Because induction of antibody responses in this tissue is important for protection against mucosally transmitted diseases, such as HIV and *Chlamydia*, anti-HA IgG1 and IgA responses in vaginal lavages collected at 1 week after the second IM vaccinations were measured. The highest vaginal anti-HA IgG1 responses was observed in the mice vaccinated with HA+VA+MO, HA+VE+MO, and HA+VE+cat+MO (FIG. 4). Moreover, the only group that showed enhanced anti-HA IgA responses compared to HA in PBS alone, was the group vaccinated with VA+MO (FIG. 5). These data indicate that combinations of the MO with VA, VE, cat result in induction of enhanced serum IgG1, IgG2a, as well as vaginal IgG1 and IgA.

Example 4

TH1, TH2, and Treg Responses Following Intramuscular (IM) Injections

TH1, TH2 and Treg Responses After Second IM Vaccination with HA.

TH1 (IFNγ), TH2 (IL-5) and Treg (IL-10) responses in splenocytes prepared at one week after the second IM vaccination and activated ex vivo overnight with HA was determined. Enhanced IFNγ responses compared to that of mice injected with HA in PBS alone were detected in the groups of mice vaccinated with HA+MO, with further enhancement when MO was mixed with other components (FIG. 6). The highest amount of IFNγ was detected in the group vaccinated with MO+cat (FIG. 6). While the groups vaccinated with VC+MO, MO alone, VE+cat+MO, and VE±MO showed enhanced IFNγ responses compared to HA alone, the responses were lower than the group vaccinated with MO+cat (FIG. 6). These data suggest that vaccinations with VA and cat+MO induced the highest TH1 responses. In contrast to TH1 responses, TH2 (IL-5) responses were only enhanced following vaccinations with VA or VE, as the IL-5 responses in the groups vaccinated with HA alone in PBS were generally high. Interestingly, vaccinations with MO plus VA, VC, VE and VE+cat reduced IL-5 responses, while vaccinations with cat+MO induced higher IL-5 responses than vaccinations with cat, but at comparable level as vaccination with HA in PBS alone (FIG. 6). Importantly, the IL-10 Treg suppressive responses mostly correlated with the poor serum IgG, or splenic IFNγ or IL-5 responses, in that the highest IL-10 responses were measured in the group vaccinated with HA in PBS alone (FIG. 6). These data indicate that IM vaccinations with cat+MO induced the most well balanced TH1, and TH2 with a lack of Treg responses.

Example 5

Immune-Modulation Following Intranasal (IN) and Sublingual (SL) Vaccinations

Materials and Methods
Adjuvants and Vaccine Preparations.

The HIV-1 gp120$_{cn54}$ protein was obtained from the NIH AIDS Research and Reference Reagents Program and was used at the dose of 5 μg per mouse. Vitamin A (Retinoic acid, Sigma-Aldrich; Cat# R2625) and Catechin Hydrate (Sigma-Aldrich, C1251) were dissolved in 200 proof absolute ethanol (Sigma-Aldrich, Cat#459844). The stock concentration was 3 μg/μl for Vitamin A (VA), 50 μg/μl for Catechin Hydrate (Cat). Mustard seed oil (MO) was purchased from Botanic Oil Innovations inc. (Spooner, Wis.). Allyl isothiocyanate (AIT) was purchased from Sigma Aldrich (Cat# W203408-500G-K). The amount used for each dose of vaccination was 30 μg for Vitamin A, 120 μg for Cat, and 1 μl for AIT. The total volume for each dose was 40 μl and was adjusted with Dulbecco's phosphate buffered saline (Cat#21-030-CV). All components used in the vaccine including vitamin A, Cat, Tween-20, MO, and PBS were tested for endotoxin with a Genscript kit (Piscataway, N.J. 08854; Cat# L00350) and the endotoxin content in each component was found to be less than 0.005 EU/ml. All vaccines were prepared in endotoxin free 2.0 ml tubes (Eppendorf biopur safe-lock microcentrifuge tubes). Tween®-20 (Sigma, Cat# P1379) was added to all groups at a final concentration of 0.1%. The combinations with MO were emulsified by repeatedly withdrawing-releasing for at least 15 times using BD's ½ CC ½ In. 27G tuberculin syringes (Cat#305620). The volume total dose volume per mouse for each combined intranasal/sublingual (IN/SL) vaccination was 38.8 μl, i.e. 19.4 μl for IN and 19.4 μl for SL routes. A group of three female BALB/c mice were vaccinated with HIVenvgp120$_{cn54}$+MO+VA+Cat+AIT (Group 1). Another group of three female BALB/c mice were vaccinated with HIVenvgp120$_{cn54}$ in PBS alone. The mice in both groups were: at 6-8 weeks of age. The two groups of mice received the combined IN/SL vaccinations twice at 2 weeks intervals. Serum and vaginal lavages were collected at 2 weeks after the second vaccination.

The mice were maintained according to IACUC guidelines in the vivarium of Murigenics Inc. (Vallejo, Calif. 94592). Before the first vaccination, the mice were anesthetized with isoflurane, for simultaneous intra-nasal (IN) and sublingual (SL) vaccinations, whereas for the second vaccination the mice were not anesthetized for IN administrations.

Test of Serum Antibodies by ELISA.

The mice were bled retro-orbitally at two weeks after the second vaccination. Sera were stored at −20° C. To measure anti-HIV gp120$_{cn54}$ IgG1 and IgG2a titers nunc Maxisorp® 96-well microplates were coated overnight with 2 μg/ml of the HIV gp120$_{cn54}$ protein in PBS (100 μl per well) at 4° C. After washing 4 times with PBS-T (0.02% Tween-20 in PBS), the plates were blocked with 200 μl blocking solution (1% goat serum, 0.02% Tween-20 in PBS) for 1 hour at room temperature. The serum samples were diluted 1/600 in the blocking solution initially and 3-fold serial dilutions were made in each column of 96-well microplates for each sample. Column 1 was used as blank. Negative control sera were from naïve mice. After addition and dilution of the serum samples, the plates were incubated for 2 hours at room temperature. The plates were then washed 5 times with PBS-T followed by addition of 100 μl goat anti-mouse IgG1-HRP conjugate (Southern Biotech, Cat# 1070-05) diluted 1/8000 in blocking solution. The plates were incubated for 1 hour at room temperature. After washing 5 times with PBS-T, 100 μl TMB substrate was added for color development. The color development was stopped in about 15-30 minutes by addition of 100 μl of 1N sulfuric acid. The plates were read at 450 nm using a microplate reader (Molecular Devices). The cutoff value was determined as two and half times of the background value (average value of blank wells). The titer of each serum sample was calculated automatically using the software based on log-logit curve. For IgG2a titration, all the procedures and reagents were the same as for IgG1 ELISA except for the secondary antibody conjugate. A goat anti-mouse IgG2a-HRP conjugate (Southern Biotech, Cat#1080-05) diluted 1/8000 was used. For IgA titration, the procedures and reagents used were the same as above except that the serum samples were diluted initially at 1/20 followed by 3-fold serial dilutions in each column and a goat anti-mouse IgA-Biotin (Southern Biotech, Cat#0106-08) diluted 1/8000 was used. The goat anti-mouse IgA-Biotin was detected using avidin-HRP.

Test of IgG1 and IgA in Vaginal Lavages by ELISA.

Vaginal lavages of about 100 μl were collected from individual mouse using a pipetman by aspirating about 100 μl PBS inside the vagina several times. The vaginal lavages were kept on dry ice for later use. Vaginal lavages were thawed and vortexed followed by centrifugation at 3000×g for 5 minutes. The vaginal lavages were tested for IgG1 and IgA by ELISA. The ELISA tests were performed in a similar way to that described for serum IgG1 and IgA above except that the initial dilution for both IgG1 and IgA was 1/3 followed by 3-fold serial dilutions. The tests also employed the PerkinElmer ELAST® ELISA Amplification System described above to increase sensitivity as per manufacturer's protocols.

Results.

At two weeks following two combined intra-nasal and sublingual vaccinations, serum IgG1 anti-HIVgp120 responses were enhanced an average of 198 fold in mice vaccinated with HIVgp120$_{cn54}$ in MO+VA+cat+AIT compared to the mice vaccinated with HIVgp120$_{cn54}$ in PBS alone (FIG. 7). Moreover, serum IgG2a anti-HIVgp120 responses were also enhanced (FIG. 7). There was also an enhancement of both IgG1 and IgA titers in vaginal lavages in mice vaccinated with HIVgp120$_{cn54}$ in MO+VA+cat+AIT compared to the mice vaccinated with HIVgp120$_{cn54}$ in PBS alone (FIG. 8).

Example 6

Immune-Modulation by IN/SL and IM Vaccinations

Materials and Methods

Groups of 3 female BALB/c mice each at 6-8 weeks of age were vaccinated with HIVenvgp120cn54 only in PBS or with HIVenvgp120cn54+MO+VA+Cat+AIT two times IN/SL route followed by two times IM.

Before the first vaccination, the mice were anesthetized with isoflurane, for simultaneous intra-nasal (IN) and sublingual (SL) vaccinations, whereas for the second vaccination the mice were not anesthetized for IN administrations. The doses of catechin and VA were as described above for IM vaccinations with HA, i.e., 120 μg and 30 μg, respectively. The dose of HIVgp120 was 5 μg for the IN/SL vaccinations and the first IM vaccination and 2.5 μg for the second (final) IM vaccination. The dose of AIT was 1 μl. MO was used at 50% v/v for both IN and IM vaccinations. Thus, the following groups of mice received two combined IN/SL, followed by two IM vaccinations at 2 weeks intervals:

Group 1: HIVenvgp120cn54+MO+VA+Cat+AIT

Group 2: HIVenvgp120cn54 only in PBS

Serum and vaginal lavages were collected at 1 week after the 4th and final vaccination, and gp120-specific IgG1, IgG2a and IgA were measured by ELISA.

Results.

IgG1, IgG2a and IgA responses in serum were markedly enhanced in the group of mice vaccinated with HIVenvgp120cn54+MO+VA+Cat+AIT compared to the group of mice vaccinated with HIVenvgp120cn54 only in PBS (FIG. 9).

IgG1 and IgA responses in vaginal lavages were also next determined. IgG1 and IgA responses in vaginal lavages were markedly enhanced in the group of mice vaccinated with HIVenvgp120cn54+MO+VA+Cat+AIT compared to the group of mice vaccinated with HIVenvgp120cn54 only in PBS (FIG. 10). These data show markedly enhanced serum and vaginal anti-gp120 antibody responses and strongly support the immune-enhancing capacity of MO+VA+Cat+AIT for induction of both vaginal and systemic humoral immunity against the HIV-1gp120 surface glycoprotein.

Example 7

Adjuvant Composition with Antigen for Administration to a Human Subject

An example of an adjuvant composition that includes a pharmaceutically acceptable vegetable oil carrier, AIT, a flavonoid, and vitamins A, E and C is provided in Table 3 below:

TABLE 3

| Component | Amount |
| --- | --- |
| Mustard Oil | 3-80% vol/vol |
| Vitamin A[1] | 0.1-100 mg |
| Vitamin E[2] | 0.1-100 mg |
| Vitamin C[3] | 0.1-2000 mg |
| Catechin hydrate[4] | 0.1-2000 mg |
| Emulsifier[5] | 0.1-7% w/w |
| Allyl Isothiocyanate | 0.001-10 mg |

The above composition may include one or more of the components shown in Table 4 below:

TABLE 4

| Component | Amount |
|---|---|
| Antigen[6] | 0.01-10 mg |
| PBS | 1-50% vol/vol |
| Gelatin | 1-20 mg |
| Antibiotics[7] | 0.1 pg-30 μg |
| Sorbitol | 1-20 mg |
| Sucrose[8] | 1-100 mg |
| Hyaluronic Acid[9] | 1-30% w/w |
| Beeswax | 1-50% w/w |

[1]Vitamin A may be provided as carotene, beta-carotene, retinoic acid, retinyl palmitate, or a derivate or slat thereof;
[2]Vitamin E may be provided as alpha-tocopherol or a derivate or slat thereof;
[3]Vitamin C or a derivate or slat thereof,
[4]Catechin hydrate or nother flavonoid,
[5]Emulsifier may be lecithin, sorbitans, polysorbates;
[6]envelope gp120 or influenza hemmagglutinin proteins,
[7]neomycin or polymyxin B,
[8]sucrose, lactose or another sugar,
[9]Hyaluronic acid or its derivatives (HYAFF) or polyethylene oxide homopolymers or chitosan.

A composition that includes (50% v/v mustard oil, 0.1% Tween (polysorbate), 50% aqueous phase v/v), the microparticle/micelle size in the emulsified composition ranges from 0.1 μm-5 μm in size with the largest at around 5 μm, the smallest at around 0.1 μm, and the majority (70-80%) ranging between 0.5-1 μm.

As used in herein vol/vol refers to the volume of a component in the total volume of the adjuvant composition. As used in herein w/w refers to the amount by weight of a component in the total weight of the adjuvant composition.

What is claimed is:

1. A composition comprising:

free mustard oil; and at least one substance selected from the group consisting of a catechin and vitamin A.

2. The composition of claim 1, wherein the composition comprises said catechin.

3. The composition of claim 1, wherein the composition comprises said vitamin A.

4. The composition of claim 1, wherein the composition comprises said catechin and said vitamin A.

5. The composition of claim 1, further comprising vitamin E.

6. The composition of claim 1, further comprising vitamin D.

7. The composition of claim 1, further comprising vitamin C.

8. The composition of claim 1, further comprising allyl isothiocyanate.

9. The composition of claim 1, further comprising an antigen.

10. A method of enhancing an immune response in a subject, the method comprising administering the composition of claim 1 to said subject.

11. The method of claim 10, wherein the subject is a mammal.

12. The method of claim 10, wherein said administering is by a route selected from the group consisting of: intranasal, pulmonary, sublingual, oral, buccal, intra-vaginal, intra-rectal, ocular, intradermal, transdermal, intra-tracheal, transdermal, transcutaneous, subcutaneous, intra-venous, intra-peritoneal, and intramuscular.

13. A method of making the composition of claim 2, the method comprising admixing said free mustard oil and said catechin.

14. The composition according to claim 1, further comprising squalene.

15. A method of making the composition of claim 3, the method comprising admixing said free mustard oil and said vitamin A.

* * * * *